(12) United States Patent
Bierman et al.

(10) Patent No.: US 7,935,083 B2
(45) Date of Patent: *May 3, 2011

(54) ANCHORING SYSTEM FOR LUER LOCK CONNECTOR

(75) Inventors: Steven F. Bierman, Del Mar, CA (US);
Wayne T. Mitchell, Cardiff, CA (US);
Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 138 days.

This patent is subject to a terminal disclaimer.

(21) Appl. No.: 12/367,442

(22) Filed: Feb. 6, 2009

(65) Prior Publication Data

US 2009/0143744 A1 Jun. 4, 2009

Related U.S. Application Data

(63) Continuation of application No. 10/753,064, filed on Jan. 6, 2004, now Pat. No. 7,491,190, which is a continuation-in-part of application No. 10/201,866, filed on Jul. 23, 2002, now Pat. No. 6,673,046, which is a continuation of application No. 09/585,526, filed on Jun. 1, 2000, now Pat. No. 6,428,515.

(51) Int. Cl.
*A61M 5/32* (2006.01)

(52) U.S. Cl. ........................ 604/174; 604/180

(58) Field of Classification Search .......... 604/174–180, 604/283, 905

See application file for complete search history.

(56) References Cited

U.S. PATENT DOCUMENTS

| 3,046,984 A | 7/1962 | Eby |
| 3,677,250 A | 7/1972 | Thomas |
| 3,900,026 A | 8/1975 | Wagner |
| 4,082,094 A | 4/1978 | Dailey |
| 4,224,937 A | 9/1980 | Gordon |
| 4,250,880 A | 2/1981 | Gordon |
| 4,397,647 A | 8/1983 | Gordon |
| 4,826,486 A | 5/1989 | Palsrok et al. |
| 4,863,432 A | 9/1989 | Kvalo |

(Continued)

FOREIGN PATENT DOCUMENTS

WO   WO9955409   * 11/1999

(Continued)

OTHER PUBLICATIONS

Office Action dated Apr. 16, 2008 for Canadian Patent Application No. 2,413,941.

*Primary Examiner* — Matthew F DeSanto
(74) *Attorney, Agent, or Firm* — Knobbe Martens Olson & Bear, LLP

(57) ABSTRACT

An anchoring system includes a simply-structured device which permits a portion of a catheter or similar medical article to be easily anchored to a patient, desirably without the use of tape or needles and suture. An anchoring system for an elongated medical article comprises an anchor pad and a retainer mounted upon the anchor pad. The retainer includes a channel into which the medical article to be retained is placed. The retainer is attached to an anchor pad including an adhesive bottom surface, which can be attached to the patient's skin. A medical article is secured within a channel by retaining at least one axially extending member on the medical article.

20 Claims, 19 Drawing Sheets

U.S. PATENT DOCUMENTS

| | | |
|---|---|---|
| 4,997,421 A | 3/1991 | Palsrok et al. |
| 5,084,026 A | 1/1992 | Shapiro |
| 5,120,320 A | 6/1992 | Fayngold |
| 5,192,273 A | 3/1993 | Bierman et al. |
| 5,314,411 A | 5/1994 | Bierman et al. |
| 5,354,282 A | 10/1994 | Bierman |
| 5,356,379 A | 10/1994 | Vaillancourt |
| 5,456,671 A * | 10/1995 | Bierman .................. 604/180 |
| 5,755,225 A | 5/1998 | Hutson |
| 6,231,548 B1 * | 5/2001 | Bassett .................. 604/174 |
| 6,290,676 B1 * | 9/2001 | Bierman .................. 604/174 |
| 6,428,515 B1 * | 8/2002 | Bierman et al. .......... 604/174 |
| 6,673,046 B2 * | 1/2004 | Bierman et al. .......... 604/174 |
| 7,491,190 B2 | 2/2009 | Bierman et al. |

FOREIGN PATENT DOCUMENTS

WO    WO 2004/016309    2/2004

* cited by examiner

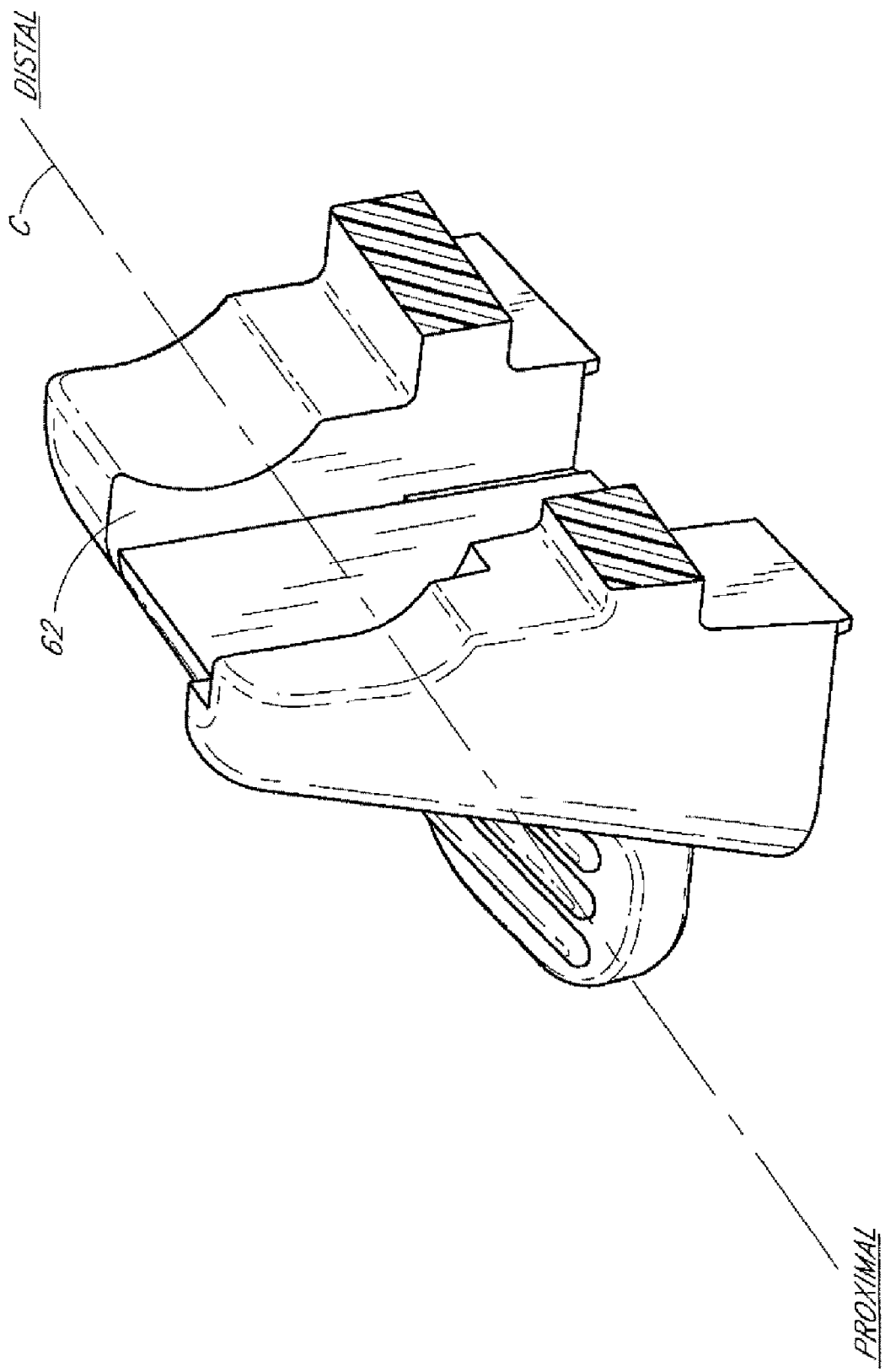

ANCHORING SYSTEM FOR LUER LOCK CONNECTOR

RELATED APPLICATIONS

This application is a continuation of application Ser. No. 10/753,064, filed Jan. 6, 2004 now U.S. Pat. No. 7,491,190, which is a continuation-in-part of application Ser. No. 10/201,866, filed Jul. 23, 2002, now U.S. Pat. No. 6,673,046, which is a continuation of application Ser. No. 09/585,526, filed Jun. 1, 2000, now U.S. Pat. No. 6,428,515, all of which are hereby expressly incorporated by reference in their entireties.

BACKGROUND OF THE INVENTION

1. Field of the Invention

The present invention relates in general to a medical article anchoring system. In one mode, the present invention involves a catheterization system that interconnects an indwelling catheter with medical tubing and securely anchors the interconnection to a patient's skin.

2. Description of the Related Art

Medical treatment of patients commonly involves the use of percutaneously inserted catheters to deliver fluids directly into the bloodstream, a specific organ or an internal location within the patient, or to monitor vital functions of the patient. For instance, short, peripherally-inserted, intra-arteriovenous catheters are commonly used to direct fluids and/or medications directly into the bloodstream of the patient.

The fluid (e.g. parenteral liquid, medication, etc.) typically drains from a container positioned above the patient to feed under gravity or is delivered via an infusion pump. The fluid flows through tubing and thence into the indwelling catheter. The catheter and the fluid tubing are commonly removably attached to each other by a conventional luer lock connection.

A luer lock connection generally includes a male luer connector with a tapered conical portion that is adapted to fit into a correspondingly shaped receptacle of a female luer connector (i.e., a hub). A spin nut is commonly disposed on the male luer connector and is rotatable relative to the tapered conical portion. The spin nut includes internal threads that are adapted to engage external threads on the female luer connector to lock together the luer connectors. When properly engaged, the conical portion fits tightly within the receptacle to produce a sealed interconnection.

A healthcare provider can experience difficulty at times breaking the seal between the engaged conical portion and the hub of the luer lock connectors when disconnecting the male luer connector from the female luer connector. In order to aid such disconnection, some luer lock connectors include spin nuts that can slide axially between a distal position, in which the spin nut can freely rotate relative to the coupled luer connectors, and a proximal position, in which the spin nut and male luer connector are rotationally locked. The rotational lock is provided to assist in breaking the sealed coupling between the corresponding surfaces of the conical portion and the hub of the interengaged luer lock connectors.

An example of this type of luer lock connector is described in U.S. Pat. No. 5,620,427, which issued Apr. 15, 1997 to Werschmidt et al. (referred to below as "the '427 patent"). The disclosed connector provides tapered engagement surfaces providing a gradual frictional engagement when tightening the spin nut to minimize inadvertent reverse rotation and loosening of the spin nut. Also, a plurality of axially extending splines for engagement with a plurality of inwardly, radially directed ribs on the spin nut allow positive rotationally locking of the spin nut and the male luer connector when the spin nut is in a proximal position. The spin nut, when locked with the male luer connector, provides greater leverage to produce more torque on the male luer connector to break the sealed coupling.

In common practice, a healthcare provider uses adhesive, foam or surgical tape to maintain the luer lock connector, and thus the catheter, in place on the skin of the patient. The healthcare provider wraps a thin piece of tape around the luer lock connector and then forms a "chevron" with the tape, placing the ends next to the sides of the indwelling catheter. The healthcare provider then places one piece of tape across and over the connector, forms a loop in the tubing, places another piece of tape across the tubing loop, and places yet an additional piece of tape over the catheter hub and the tubing section that has been looped around and extends next to the indwelling catheter. This step forms a safety loop in the tubing so that any tension applied to the tubing does not directly pass to the catheter cannula, but rather is absorbed by the slack of the safety loop. Subsequently, the healthcare provider typically covers the insertion site and the indwelling catheter with a transparent dressing.

The entire taping and dressing procedure takes several minutes of the healthcare provider's valuable time. In addition, the catheterization process often requires relatively frequent disconnection between the catheter and the fluid supply tube, as well as dressing changes. For instance, intravenous catheterization is frequently maintained for several days, depending upon the condition of the patient. The tubing is generally replaced every 48 to 72 hours in order to maintain the sterility of the fluid and the free-flow of the fluid through the tubing. A healthcare provider thus must frequently change the tubing and re-tape the connection. The healthcare provider also must frequently clean the insertion site about the indwelling catheter and change the dressings. Moreover, the tape, which secures the catheter to the skin of the patient, often covers the cannula insertion point. The healthcare provider must remove the tape to inspect the insertion point for inflammation or infection, and must then repeat the above-described taping procedure.

The healthcare provider thus uses a great deal of valuable time applying, removing and reapplying tape. The frequent application and removal of the tape also commonly excoriates the patient's skin about the insertion site.

In addition, the traditional method of intravenous catheter securement—surgical tape and transparent dressings alone—have not always prevented catheter migration and/or dislodgment. Taped intravenous catheters are also easily pulled out during a "routine" dressing change, especially by inexperienced healthcare providers. And if the catheter migrates too far or dislodgment occurs, the healthcare provider must replace the catheter, thus exacerbating the time and expense required to maintain the intravenous feed. Such catheter re-starts also poses the risk of needle stick to the healthcare provider.

Prior securement methods have not served the patient as well. Surgical tape or foam strips are uncomfortable. Many patients also do not rest comfortably and worry about catheter dislodgment when they move, when only tape and a dressing secure the catheter in place.

Several additional drawbacks result from the use of tape to stabilize the catheter. One is contamination. Healthcare providers often tear off small strips of tape and place them on the hand rail on the patient's bed. Clostridium and other bacteria commonly exist on these surfaces and can be transferred to the patient's skin in the proximity of the insertion site.

In addition, tape securement requires the healthcare provider to handle the tape while wearing protective latex gloves. Tearing adhesive tape tends to produce microscopic and/or visible holes in the gloves and thus destroys glove barrier protection.

A number of catheter securement systems have been developed to obviate the need for frequent application of tape to secure a catheter to a patient. One such securement system is disclosed in U.S. Pat. No. 5,456,671, issued Dec. 10, 1995, to Steven F. Bierman, M. D. (hereinafter referred to as "the '671 patent"). The preferred form of the securement system disclosed in this patent involves a retainer having a plurality of lateral slots. Each slot has a similar size and is designed to receive a collar of an associated catheter connector or adaptor. The cooperating structure of the connector and the retainer, i.e., the slots and the collar, arrests longitudinal movement of the connector through the retainer, and permits quick insertion of the connector into the retainer. The healthcare provider need not worry about the rotational orientation of the connector above the retainer and only need to align coarsely the collar of the connector above the series of slots before pushing the connector into the retainer.

The retainer, which is disclosed in the '671 patent, does not work as well with the connector disclosed in the '427 patent. As noted above, the connector disclosed in the '427 patent has a plurality of axially extending splines that are spaced around a portion of the circumference of the connector's tubular body. At least one of these splines has a longer length than that of at least one of the other splines. Because the slots in the illustrated form of the retainer disclosed in the '671 patent all have the same size, the rotational orientation of the connector becomes important before the connector is inserted into the retainer. Insertion of the connector into the retainer thus requires more effort and care, thereby decreasing the ease of using the securement system disclosed in the '671 patent.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

In accordance with one aspect of the present invention, an anchoring system provides releasable securement of a medical article (i.e., a catheter) to the patient. The releasable engagement is achieved by cooperation between a retainer, a connector or a section of the medical article, and an anchor pad. This cooperation allows the medical article to be disconnected from the anchoring system, and from the patient, for any of a variety of known purposes. For instance, a healthcare provider may want to remove the medical article from the anchoring system to ease disconnection of the medical article from the patient or to clean the patient. The disengagement of the medical article from the anchoring system, however, can be accomplished without removing the anchoring system from the patient.

The present anchoring system also arrests movement of the medical article and/or the connector with respect to the anchoring system. Transverse, lateral and longitudinal (i.e., axial) movement is generally inhibited by the holding effect provided by the retainer. That is, the retainer generally surrounds the connector and/or section of the medical article while recesses within the retainer capture projections on the connector or the medical article.

Sturdy anchoring of the medical article thus is achieved without the use of surgical tape. Additionally, the anchoring system is attached to the patient only once for most intravenous courses. Although the fluid supply tubing may be replaced every 24 to 48 hours for intravenous catheterization, the components of the present anchoring system remains in place through multiple dressing and supply tubing changes. Thus, surgical tape need not be applied and removed from the patients' skin on multiple occasions.

In one mode, the anchoring system is configured to securely anchor a luer lock connector of the type that includes an elongated tubular body with at least first and second axially extending splines. The second axially extending spline has a longer longitudinal length than that of the first axially extending spline, and the tubular body extends in a longitudinal direction from a proximal end to a distal end. The connector disclosed in U.S. Pat. No. 5,620,427 is an example of this type of lure lock connector.

The anchoring system comprises a retainer and an anchor pad. The retainer is affixed to one side of the anchor pad, and the other side of the anchor pad includes an adhesive layer that is adapted to secure the anchor pad and the retainer to the skin of the patient.

One aspect of the present invention is a retainer for securing a medical device having an elongated tubular body having a proximal end and a distal end, and including at least first and second axially extending splines, the second axially extending spline having a greater longitudinal length than the first axially extending spline. The retainer comprises a body having a base surface for attachment to an anchor pad, a proximal end portion and a distal end portion, and a channel extending through at least the proximal and distal end portions. The body further comprising an opening located in the proximal end portion and having a diameter less than a diameter of the channel and a pair of longitudinally opposed abutment surfaces, each of which is formed on one of the proximal and distal end portions, the abutment surfaces lying generally normal to the central axis of the channel and being spaced longitudinally apart from each other by a distance that generally corresponds to the longitudinal length of the second spline of the tubular body.

Another aspect of the present invention is a retainer for securing a medical device including an elongated tubular body having a proximal end and a distal end, and including at least one axially extending spline. The retainer comprises a body that comprises a base surface for attachment to an anchor pad, a proximal end portion and a distal end portion, and a channel extending through at least the proximal and distal end portions. The body further comprises an opening located in the proximal end portion and having a diameter less than a diameter of the channel and a pair of longitudinally opposed abutment surfaces, each of which is formed on one of the proximal and distal end portions, the abutment surfaces lying generally normal to the central axis of the channel and being spaced longitudinally apart from each other by a distance that generally corresponds to the longitudinal length of the spline of the tubular body.

The retainer includes a body having first and second end portions and an intermediate portion. The intermediate portion includes a pair of flexible walls. A channel extends through at least the first and second end portions and through the intermediate portion of the body between the flexible walls. The flexible walls are deflectable away from a central axis of the channel. The first end portion defines a first abutment surface that lies generally normal to the central axis of the channel, and the second end portion defines a second abutment surface that lies generally normal to the central axis of the channel. The second abutment surface generally opposes the first abutment surface. The first and second abutment surfaces are spaced from each other by a distance greater than the longitudinal length of the second spline of the tubular body. At least one of the flexible walls includes third and forth abutment surfaces that lie generally normal to the central axis of the channel and that generally oppose each other. The third and fourth abutment surfaces are spaced apart from each other by a distance that generally corresponds to the longitudinal length of the first spline of the tubular body.

In a preferred form, the distance between the first and second abutment surfaces generally corresponds to a longitudinal length measured between the proximal end of the connector tubular body and a distal end of the second spline. The first end portion also includes a fifth abutment surface positioned distal of the first abutment surface. The fifth abutment surface is distanced from the second abutment surface by a distance substantially equal to the longitudinal length of the second spline. Additionally, the other flexible wall also includes abutment surfaces that correspond to the third and fourth abutment surfaces.

The retainer arrests longitudinal movement of the connector with respect to the anchoring system in at least a distal direction, at least in part by retaining one or more of the splines. For example, with respect to a retainer configured in accordance the preferred mode, the second spline is captured between the second and fifth abutment surfaces when the connector is inserted into the retainer with the second spline oriented downwardly (i.e., facing the retainer channel) or to one side. With the connector so situated, the second spline causes the corresponding flexible wall to deflect laterally outward and occupies the space between the second and fifth abutment surfaces. When the retainer is inserted into the retainer with the second spline oriented upwardly (i.e., facing away from the retainer channel) or downward, the first spline is captured between the abutment surfaces on one of the flexible walls, i.e., between the third and forth abutment surfaces. Accordingly, at least one spline is captured between a corresponding pair of abutment surfaces regardless of the orientation of the longer second spline (e.g. oriented upwardly, downwardly or to one side) when the connector body is inserted into the retainer. The corresponding pair of abutment surfaces thus arrest longitudinal movement of the connector in both the proximal and distal directions along the longitudinal axis.

Additionally, the first abutment surface lies just proximal of the proximal end of the connector body when the retainer receives the connector, no matter how the second spline is situated. The first abutment surface thus also inhibit longitudinal movement of the connector in the proximal direction. For this reason, it is understood that one or more of the distal facing abutment surfaces (i.e., the third and fifth abutment surfaces) can be omitted from the retainer. It also is understood that the first abutment surface can be omitted from the retainer where the retainer includes one or more of the other distal facing abutment surfaces (e.g., the third abutment surface and/or the fifth abutment surface) to arrest movement in the proximal direction. Thus, in the preferred mode of the retainer, at least two of these distal facing abutment surfaces (i.e., the first, third and fifth abutment surfaces) redundantly inhibit longitudinal movement of the connector in the proximal direction at all times when the connector body is inserted into the retainer channel.

The anchoring system thus is designed for a healthcare provider to quickly insert the connector into the retainer, without requiring precise alignment or positioning of the connector on the anchoring system. That is, the healthcare provider need not be concerned with the rotational orientation of the catheter body before inserting it into the retainer as the retainer can properly receive the connector with the longer second spline lying at any position (e.g., upward, downward, or to one side relative to the retainer channel).

The retainer also can be configured to interact with a connector that has splines with staggered positions along the length of the connector body. For example, a connector can have splines of the same length, but a distal end of one of the splines lies closer to a distal end of the connector than a distal end of another spline. The present retainer can be configured to hold such a connector. The ability of one retainer wall section, which includes at least one abutment surface, to deflect relative to the adjacent retainer wall sections, which each also include at least one abutment surface, enables the retainer to accommodate a connector having splines with distal end positions differing along the length of the connector body, regardless of whether such differing distal end positions occur because of differing lengths, a staggered arrangement, or a combination of the two.

In addition, the retainer can be configured to interact with a connector having splines of equal lengths and at the same axial location along the connector's length. In such case, the retainer need not include all five abutment surfaces (e.g. it could include only two or three abutment surfaces).

In a variation, a catheter hub or body can include splines or other projections, and the retainer can be configured to receive a section of the catheter (e.g. the catheter hub) and to capture one or more of the corresponding splines or projections to arrest axial movement of the catheter.

Another aspect of the present invention involves an anchoring system for a medical article. The anchoring system comprises an anchor pad, which has upper and lower sides, and a retainer. The retainer is disposed on the upper side of the anchor pad. The lower side of the anchor pad includes an adhesive surface to secure the retainer to the skin of a patient. The anchor pad also includes at least one elongated extension with an adhesive undersurface. The extension is adapted to be rolled upon itself around a portion of the medical article. In this manner, the extension can be used to secure a section of the medical article to the anchor pad. The secured section can thus, for example, form a safety loop along the length of the medical article.

In accordance with an additional aspect of the present invention, a catheterization system comprises a catheter connector, a retainer and an anchor pad. The connector includes an elongated tubular body that extends in a longitudinal direction from a proximal end to a distal end and has at least first and second axially extending splines disposed on and extending radially from the tubular body. The second axially extending spline has a longer longitudinal length than that of the first axially extending spline. In one mode, the catheter connector is located at the proximal end of the catheter and, in another mode, the catheter connector is located at a distal end of a fluid tube (e.g., a fluid delivery or drainage tube) which is to be coupled to a catheter.

The retainer includes a body and channel that extends longitudinally through at least a portion of the body. The body defines at least first, second, third and fourth abutment surfaces positioned along the channel and extending laterally therefrom so as to lie generally normal to an axis of the channel. The second and third abutment surfaces are arranged between the first and fourth abutment surfaces in the longitudinal direction. The first and fourth abutment surfaces are spaced apart by a distance that is at least a long as the longitudinal length of the second spline, and the second and third abutment surfaces are spaced apart by a distance that is substantially equal to the longitudinal length of the first spline.

The anchor pad includes upper and lower sides. The retainer is disposed on the upper side of the anchor pad, and the lower side of the anchor pad including an adhesive surface to secure the retainer to the skin of a patient.

Another aspect of the present invention involves an anchoring system for securely anchoring a medical article to a patient. The anchoring system comprises a retainer including a body and a channel that extends longitudinally through at least a portion of the body. The body defines at least first, second and third abutment surfaces positioned along the channel. The first, second and third abutment surfaces extend generally laterally from the channel. The second abutment surface is laterally moveable relative to one of the first and third abutment surfaces and is disposed between the first and third abutment surfaces.

A further aspect of the present invention involves an anchoring system for securely anchoring to a patient a luer lock connector of the type having an elongated tubular body that extends in a longitudinal direction from a proximal end to a distal end, and that includes at least first and second axially extending splines. The anchoring system comprises a retainer including a body having first and second end portions and an intermediate portion between the first and second end portions. The intermediate portion includes a pair of flexible walls. Each wall is deflectable relative to the first and second end portions. A channel extends through at least the first and second end portions and through the intermediate portion of the body between the flexible walls. The flexible walls are deflectable away from a central axis of the channel. The first end portion defines a first abutment surface that lies generally normal to the central axis of the channel, and the second end portion defines a second abutment surface that lies generally normal to the central axis of the channel and that generally opposes the first abutment surface. At least one of the flexible walls includes a third abutment surface that lie generally normal to the central axis of the channel at a location between the first and second abutment surfaces.

In a preferred mode, the anchoring system also includes an anchor pad. The retainer is affixed to one side of the anchor pad, and the other side of the anchor pad includes an adhesive layer adapted to secure the anchor pad and the retainer to the skin of the patient. The retainer also can be secured to the patient in other ways, for example, by suturing, although this mode of securement is less preferred.

In accordance with a preferred method of securing a luer lock connector on a retainer of an anchoring system, a luer lock connector is provided that includes at least first and second splines with differing end points (i.e., differing points at which the splines end) along the length of the connector. The lure lock connector is inserted into a channel of a retainer without regard to the orientation of the splines so that the splines may be in any of a plurality of positions with respect to the retainer when inserted. The splines are in a first position of the plurality of positions with the first spline facing laterally, and are in a second position of the plurality of positions with the first spline rotated from the first position such that the second spline faces laterally. The method further involves longitudinally restraining (a) the first spline between a first pair of abutment surfaces of the retainer if the splines are in the first position, or (b) the second spline between a second pair of abutment surfaces of the retainer if the splines are in the second position. At least one abutment surface of the second pair of abutment surfaces is different from one of the abutment surfaces of the first pair of abutment surfaces.

For purpose of summarizing the invention and the advantages achieved over the prior art, certain objects and advantages of the invention have been described above. Of course, it is to be understood that not necessarily all such objects or advantages be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages taught or suggested herein. Additionally, further aspects, features and advantages of the present invention will become apparent from the detailed description of the preferred embodiment that follows.

BRIEF DESCRIPTION OF THE DRAWINGS

The invention will now be described with reference to the drawings of a preferred embodiment of the present anchoring system, which is intended to illustrate and not to limit the invention. The drawings contain the following figures:

FIG. 21 is a second isometric, cross-sectional view of the retainer of FIG. 15, taken along the 21-21 line;

DETAILED DESCRIPTION OF THE PREFERRED EMBODIMENTS

The present embodiment of the medical article anchoring system is disclosed in the context of a catheterization system, and in particular in the context of a catheterization system utilizing a luer lock connector of the type disclosed in U.S. Pat. No. 5,620,427 to Werschmidt et al. The catheterization system also can include a catheter, a tube extension set and/or dressing materials.

The principles of the present invention, however, are not limited to catheters or to the specific type of connector disclosed in the '427 patent. Instead, it will be understood by one of skill in this art, in view of the present disclosure, that the anchoring system disclosed herein also can be successfully utilized in connection with other types of luer connectors, including those with splines of equal lengths or of staggered positions along the connector body length, as noted above. In addition, it will be understood by one of skill in this art that the anchoring system disclosed herein also can be successfully utilized in connection with other types of medical articles, including other types of catheters, fluid drainage and delivery tubes, and electrical wires. For example, but without limitation, the retainer disclosed herein can be configured to secure peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein. Thus, the illustration and description of the anchoring system in connection with a catheterization system, which include a luer lock connector similar to that used in U.S. Pat. No. 5,620,427, merely exemplifies one possible application of the present anchoring system.

Figure 1:
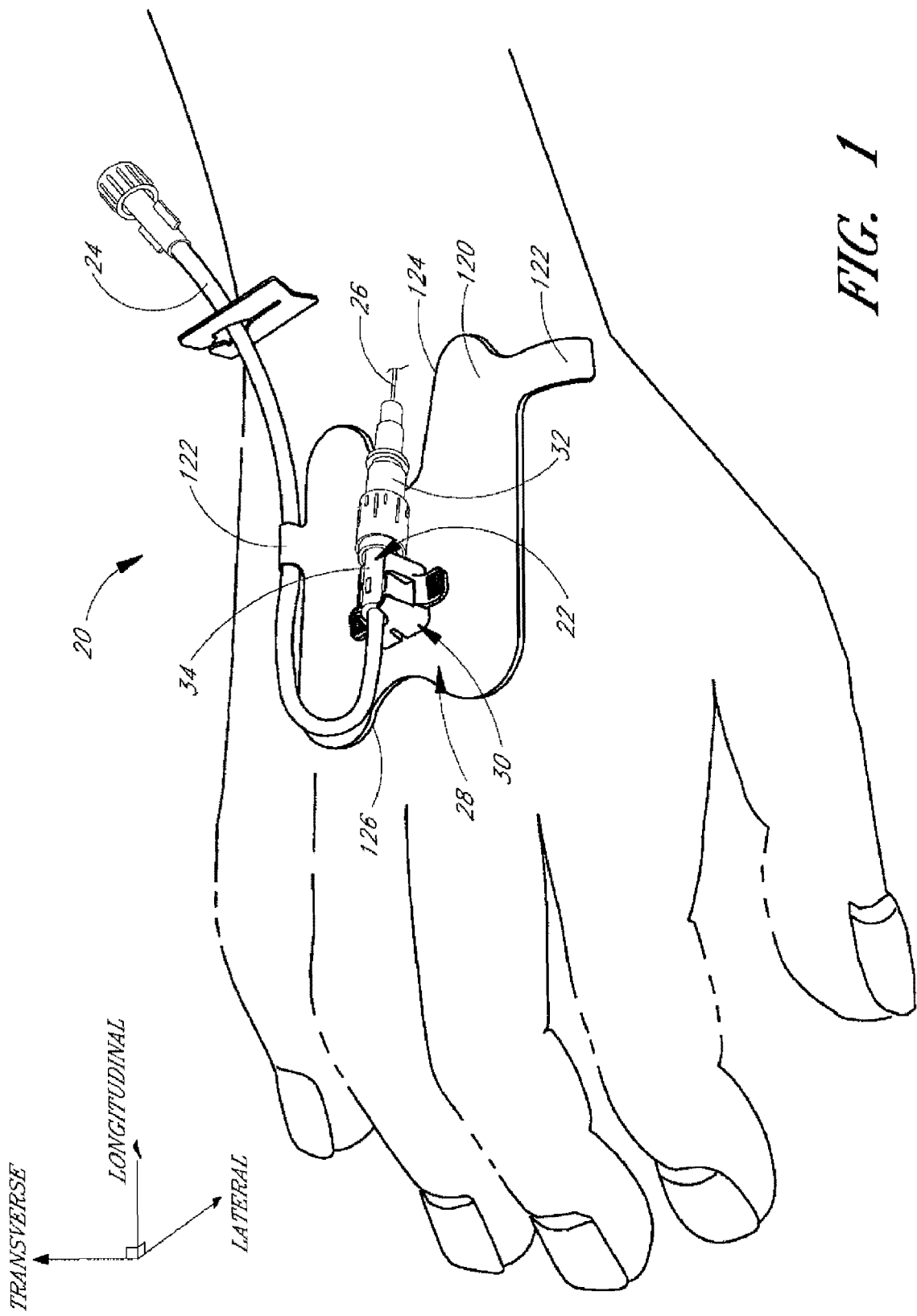
FIG. 1 is an perspective view of a catheterization system in accordance with a preferred embodiment of the present invention, being mounted on the back of a patient's hand and securing a catheter connector to the patient.

With reference now to the preferred embodiment, FIG. 1 illustrates in perspective view a catheter anchoring system 20. The anchoring system 20 cooperates with a luer lock connector 22 that securely connects a tube 24 (e.g., a fluid supply line) to an indwelling catheter 26. The cooperation between the anchoring system 20 and the connector 22 maintains the catheter 26 in the desired indwelling position.

The anchoring system 20 principally comprises a flexible anchor pad 28 having an adhesive bottom side that attaches to the skin of a patient when used. The pad 28 can be attached at any number of locations on a patient's body. Thus, although FIG. 1 illustrates the anchoring system 20 located on the back of a patient's hand, it can be used for catheterization at other locations on the patient's body, e.g. on the medial side of the wrist in connection with catheterization of a radial artery or on the anterior or posterior of the patient's torso in connection with epidural catheterization. The pad 28 supports a retainer 30. The retainer 30 in turn is configured to receive and secure in place the catheter connector 22.

To assist in the description of the components of the anchoring system, the following coordinate terms are used (see FIG. 1). A "longitudinal axis" is generally parallel to the section of the catheter 26 or connector 22 retained by the anchoring system 20. A "lateral axis" is normal to the longitudinal axis and is generally parallel to the plane of the anchor pad 28. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal", which are used to describe the present anchoring system, are used consistently with the description of the exemplifying application. Thus, proximal and distal are used in reference to the fluid supply container (not shown) attached to a fluid supply line 24. Also, the terms "top," "bottom," "upper," and "lower" are used in the context of the orientation of the anchoring system illustrated in FIG. 1, and are not intended to imply a limitation to the orientation that the anchoring system can assume on the patient. A detailed description of the catheterization system (including the present anchoring system), and its associated method of use, now follows.

Luer Lock Connector

With reference to FIG. 1, a luer lock coupling is formed between a luer lock connector 22 and a hub 32 of the catheter 22. Although the luer lock connector 22 is illustrated as being of the type disclosed in U.S. Pat. No. 5,620,427 to Werschmidt et al., which is hereby incorporated by reference, other types of connector and adaptors can be used as well with the present anchoring system 20. For instance, the catheter connector can be a luer-type connector without a spin nut. Those skilled in the art can readily select the type of connector to be used with the present anchoring system 20 and can modify the anchoring system according to the teachings of the present invention to suit the particular application (e.g. venous, arterial, epidural, peripheral, etc.).

Figure 2A:
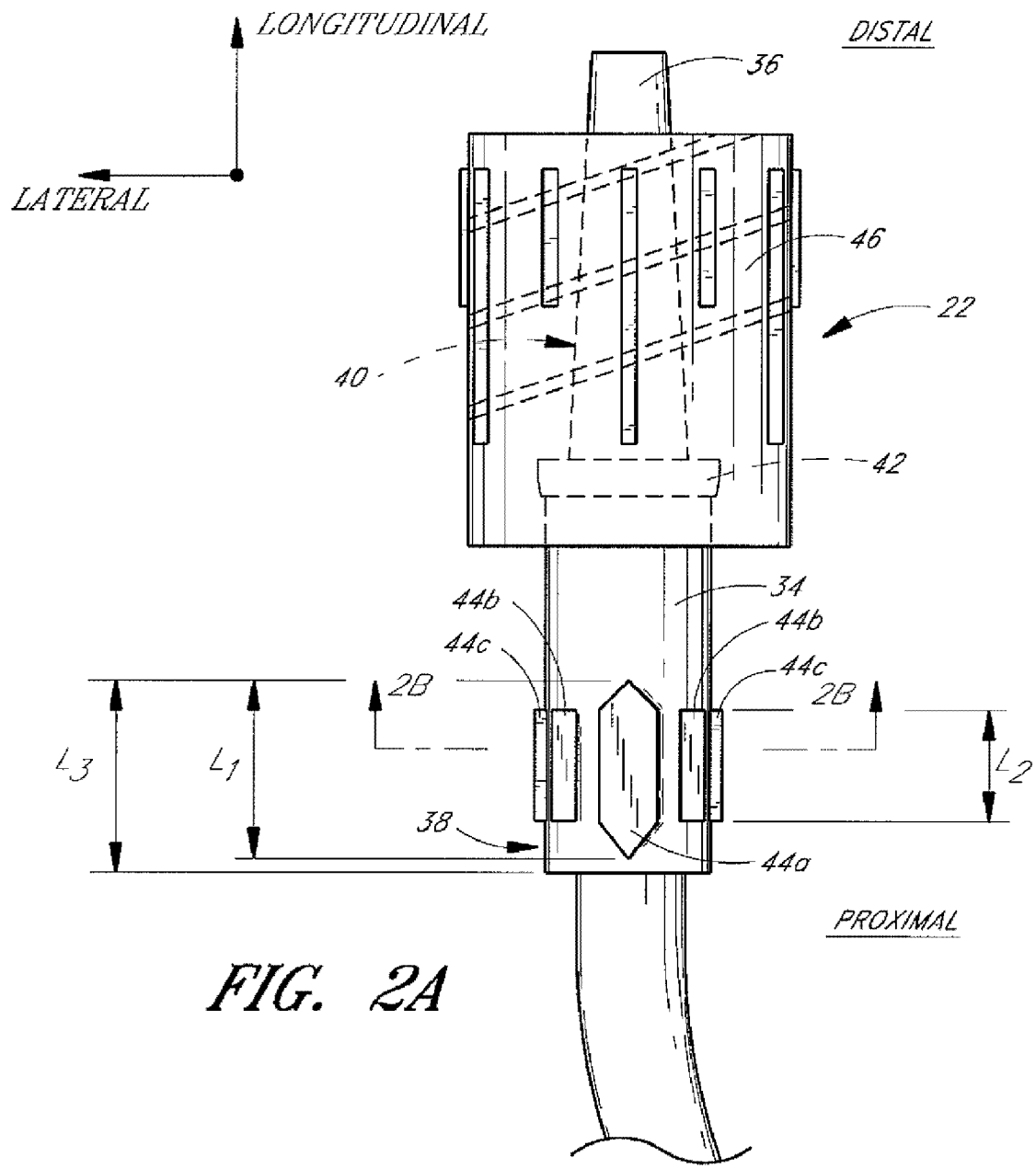
FIG. 2A is a top plan view of the catheter connector of the catheterization system illustrated in FIG. 1.

As best seen in FIGS. 1 and 2A, the connector 22 comprises a tubular body 34 defined between a distal end 36 and a proximal end 38. The proximal end 38 is adapted to receive a distal end of the tube 24. In an exemplifying embodiment, at least a portion of the fluid tube 24 is permanently attached to (e.g. embedded within) the proximal end 38 of the connector body 34.

The distal end 36 is configured to engage the proximal hub 32 of the catheter 14 (see FIG. 1) or of any luer-type female connector. In the illustrated embodiment, the distal end 36 of the connector 22 is configured as a male luer portion 40 to be inserted into a standard receptacle of a luer-type catheter hub 32. The distal end 36, however, can be configured to engage other types of catheter connectors, such as, for example, a Toughy-Bourst adaptor. As seen in FIG. 2A, the male luer portion 40 has a frusto-conical shape and extends distally from the tubular body 34. A tapered shoulder 42 is disposed between the tubular body 34 and the male luer portion 40.

A central lumen extends through the tubular body 34 and the male luer portion 40, and terminates at a distal opening at the distal end 36 of the male luer portion 40. A proximal end of the central lumen communicates with the fluid tube 24.

Figure 2B:
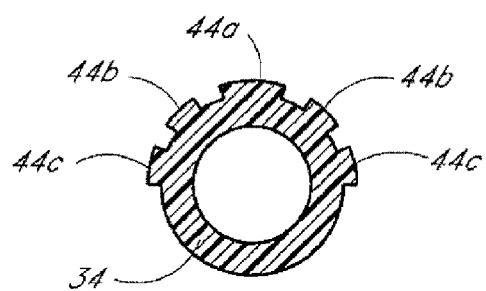
FIG. 2B is a cross-sectional view of the catheter connector taken through line 2B-2B of FIG. 2A.

With reference to FIGS. 2A and 2B, the proximal end 38 of the connector 22 includes a series of axially extending splines 44 projecting outward from the tubular body 34. In particular, the connector 22 includes at least one central, axially elongated spline 44a, a pair of intermediate splines 44b disposed on either side of the central spline 44a, and a third pair of outer splines 44c that are substantially diametrically opposed to each other. The central spline 44a lies at a position 90° apart from each outer spline 44c. The central spline 44a also has a generally rectangular shape that tapers to a point on both longitudinal ends of the rectangular body. The second and third pair of splines 44b, 44c form generally rectangular radial projections. The splines 44 are spaced around half of the circumference of the connector's tubular body 34, as best seen in FIG. 2B.

As seen in FIG. 2A, the central spline 44a has a longitudinal length $L_1$, and each spline 44b, 44c of the second and third pairs of splines has a longitudinal length $L_2$. In addition, the distal end or tip of the elongated central spline 44c is spaced from the proximal end 38 of the tubular body 34 by a longitudinal length $L_3$. In the illustrated embodiment, longitudinal length $L_3$ is longer than longitudinal length $L_1$, and $L_1$ is longer than longitudinal length $L_2$.

The connector 22 also includes a spin nut 46 disposed on its distal end 36. The spin nut 46 comprises a generally tubular sleeve having a cylindrical exterior surface, a proximal annular flange, and a series of axially extending grip rails. The spin nut 46 has three distinct interior surface regions. A first distal region includes single or multiple internal threads. The proximal end of the distal region terminates at an intermediate region comprising an anti-rotational, friction enhancing structure such as an annular internal ramp (not shown) that cooperates with the tapered shoulder. Finally, a proximal region includes a plurality of radially and inwardly directed ribs separated by channels or guideways (not shown).

The radially inwardmost edges of the inner ribs on the spin nut 46 define a circle having approximately the same diameter as the tubular body 34 of the connector 22. The ribs are so dimensioned to interfit in sliding engagement between the splines 44 along guideways. Conversely, the splines 44 extend into the channels between the ribs. The circumferential dimensions of the ribs and guideways may provide a slight interference tolerance to indicate when the spin nut 46 and tubular body 34 are rotationally locked.

Further description and alternative embodiments are described in, but not limited to, the disclosure of the U.S. Pat. No. 5,620,427 to Werschmidt et al.

Retainer

FIGS. 3 through 10 illustrate the retainer 30, which is configured in accordance with a preferred embodiment of the present invention. The retainer 30 has a body 50 that defines a central channel 52 disposed above a base surface 54. The channel 50 extends about a central, longitudinally extending axis C and has an opening 56 that faces away from the base surface 54. The proximal and distal ends of the channel 52 also open through the ends of the retainer body 50. At least a portion of the channel 52 has a lateral width that is smaller than the diameter of the connector tubular body 34, as described below in greater detail.

Figure 6:
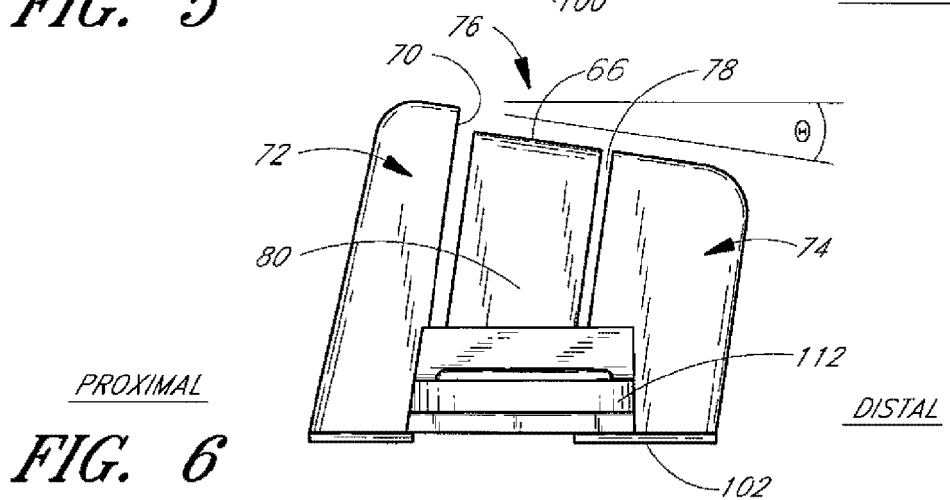
FIG. 6 is an elevational side view of the retainer of FIG. 3.

FIG. 6 illustrates that the channel axis C is desirably skewed relative to a base surface 54 of the retainer 30. An incident angle θ defined between the base surface 54 and the channel axis C preferably is less than 45°. More preferably, the incident angle θ ranges between 5° and 30°. In an exemplifying embodiment for intravenous use, the angle θ preferably equals approximately 7°. In another exemplifying embodiment for arterial use, the incident angle θ preferably equals about 22°.

Figure 3:
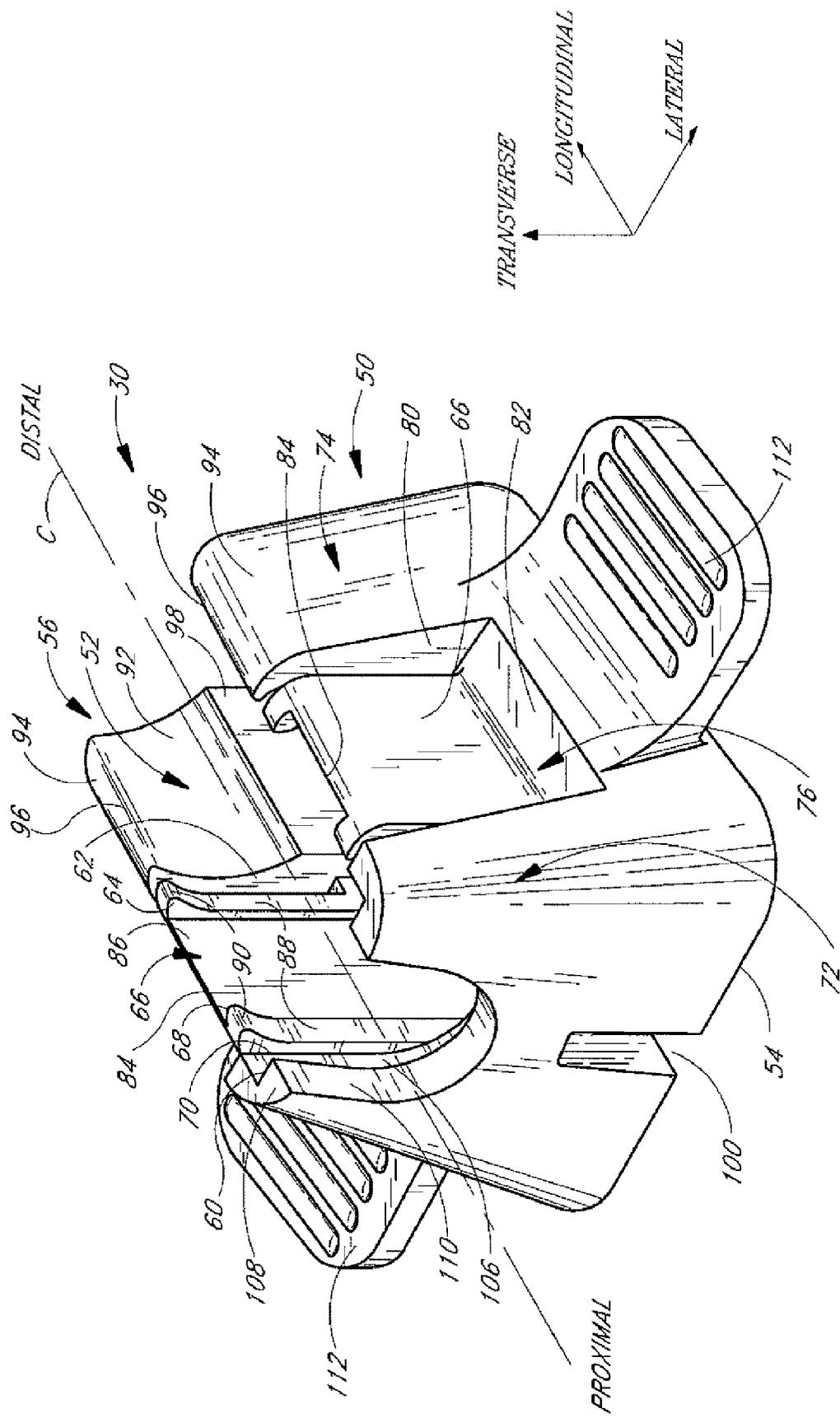
FIG. 3 is a perspective view of a retainer of the catheterization system of FIG. 1.
Figure 4:
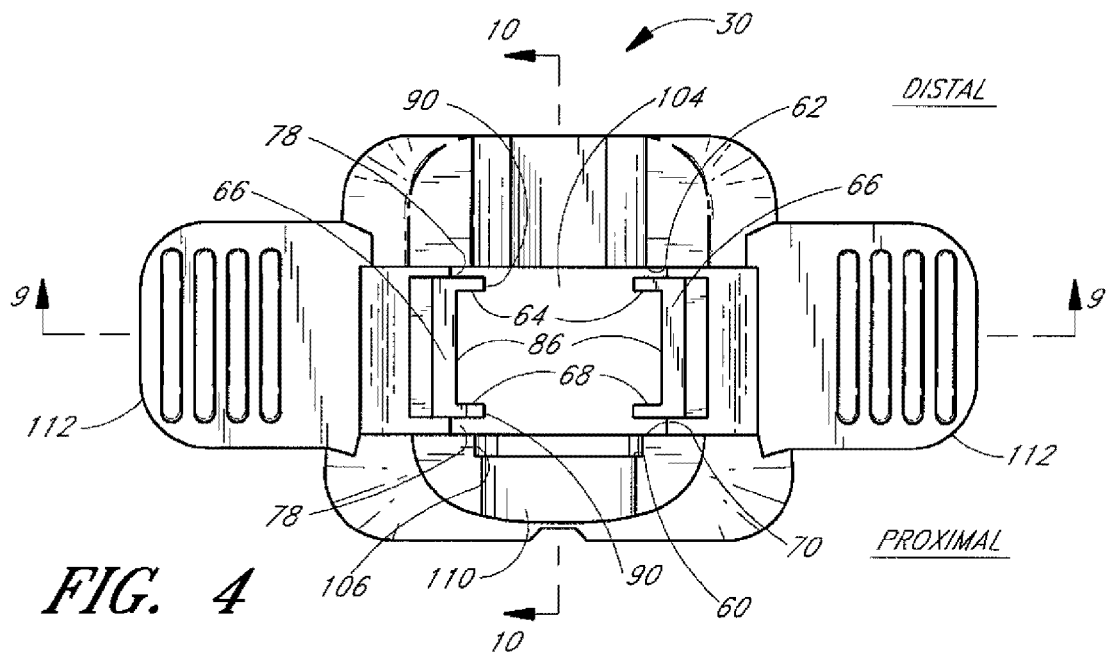
FIG. 4 is a top plan view of the retainer of FIG. 3.
Figure 10:
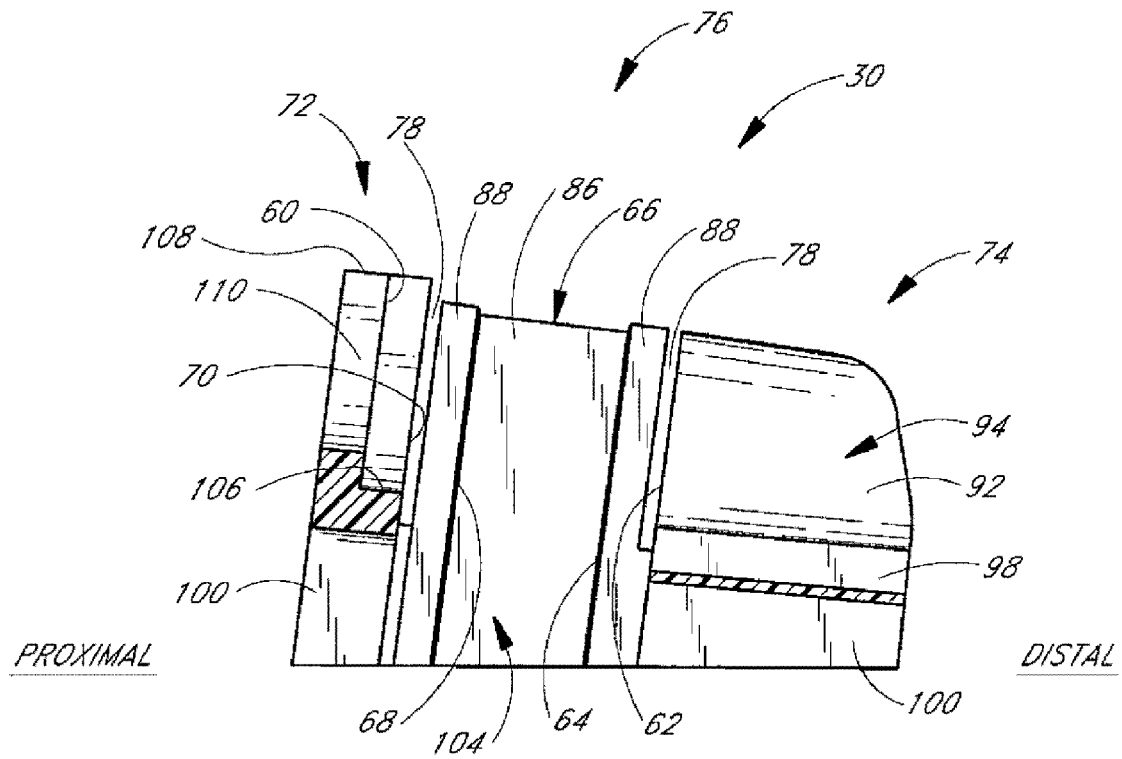
FIG. 10 is a cross-sectional view of the retainer of FIG. 4, taken along the 10-10 line.

As best seen in FIGS. 3, 4 and 10, the retainer 50 also includes a plurality of abutment surfaces the extends laterally from the channel 52. Each abutment surface lies generally normal to the central axis C of the channel 52. These abutment surfaces include a proximal-most abutment surface 60, a distal-most abutment surface 62 and an intermediate surface 64. The intermediate surface 64 lies between the proximal- and distal-most abutment surfaces 60, 62 and is defined on a flexible wall 66 so as to be movable relative to at least one of the abutment surfaces 60, 62. The proximal- and distal-most abutment surfaces 60, 62 preferably are separated by a distance that is generally equal to the longitudinal length $L_3$ between the proximal end 26 of the connector tubular body 34 and a distal tip of the central spline 44a.

In a more preferred mode, the flexible wall 66 includes two intermediate abutment surfaces: an intermediate proximal abutment surface 68 and an intermediate distal abutment surface 64. These abutment surfaces 64, 68 face each other and are spaced apart by a distance that is generally equal to the longitudinal length $L_2$ of the intermediate and outer splines 44b, 44c.

The illustrated embodiment of the retainer 30 includes an additional penult-proximate abutment surface 70 disposed between the proximal-most abutment surface 60 and the intermediate proximal abutment surface 68. The penult-proximate abutment surface 70 lies generally normal to the central axis C of the channel 52 and is distanced from the distal-most abutment 62 surface by the longitudinal length $L_1$ of the central spline 44a. In a variation of the retainer, the proximal-most abutment surface can be omitted when the retainer includes this additional abutment surface that cooperates with the proximal end of the central spline 44a.

As seen in FIG. 3, the retainer body 50 includes proximal and distal end portions 72, 74 and an intermediate portion 76. The channel 52 extends through these portions 72, 74, 76 and is open at each of its ends through end walls of the proximal and distal end portions 72, 74.

With reference to FIGS. 3, 4, 9 and 10, the intermediate portion 76 is formed by a pair of flexible walls 66 between which the channel 52 passes. Transversely extending slots 78 separate each flexible wall 66 from the adjacent proximal and distal end portions 72, 74, and an outer side of each wall 66 includes a relief 80 that reduces the lateral width of the wall 66 relative to the adjacent proximal and distal end portions 72, 74. The relief 80 extends from its base 82 to an upper edge 84 of the wall 66, and preferably has a transverse height at least as large as half the diameter of the connector tubular body 34, and more preferably, at least as large as the diameter of the connector tubular body 34. This wall structure allows the wall 66 to deflect laterally outwardly, relative to the adjacent proximal and distal end portions 72, 74 of the retainer body 50.

Each flexible wall 66 also includes an intermediate proximal abutment surface 68 and an intermediate distal abutment surface 64. These abutment surfaces 64, 68 are formed on an inner side of the wall, and in the illustrated embodiment, are disposed near the proximal and distal ends of the wall 66. Each intermediate abutment surface 64, 68 preferably extends in the transverse direction along the entire height of the wall. In the illustrated embodiment, the lateral width of each abutment surface 64, 68 also is at least as large as half the radial dimension of each spline of the second and third pairs of splines 44b, 44c, and preferably is at least as large as the radial dimension.

Each flexible wall 66 additionally has a generally flat, upstanding surface 86 defined between the opposing abutment surfaces 64, 68. End strips 88 are defined on either side of the flat surface 86. An upper end 90 of each end strip 88 curves inwardly toward a center of the channel opening 56. The radius of curvature preferably matches or at least approximates the radius of the connector tubular body 34. The upper ends 90 of the end strips 88 thus reduce the lateral width of the channel opening 56 as defined between the opposing end strip upper ends 90. In this manner, the flexible walls 66 either grip onto or at least extend over an upper section of the connector tubular body 34 to inhibit unintentional transverse movement of the connector 22 once situated within the retainer 30.

Figure 9:
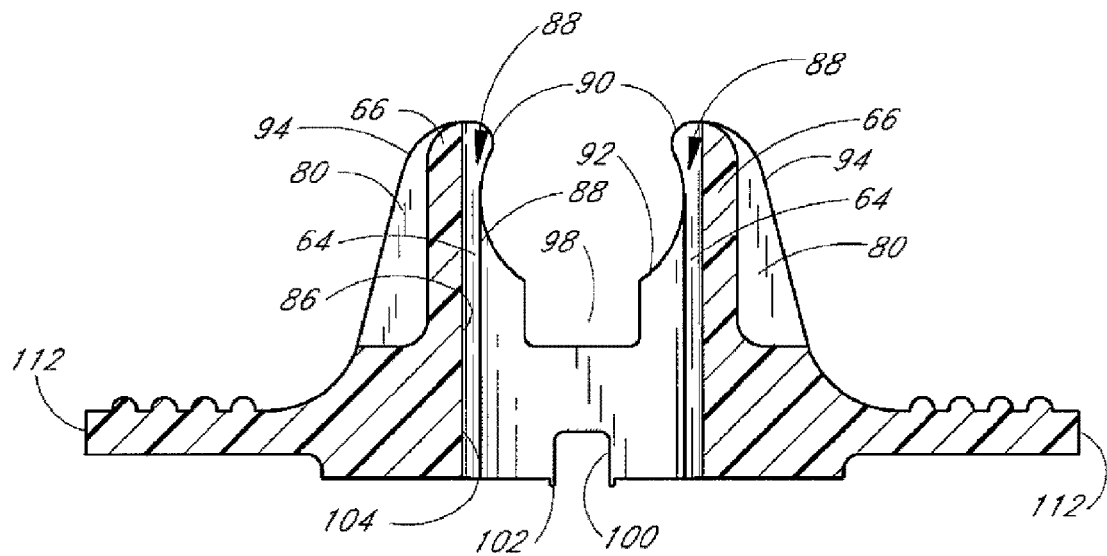
FIG. 9 is a cross-sectional view of the retainer of FIG. 4, taken along the 9-9 line.

As best seen in FIG. 9, the upper sides surfaces of the end strip upper ends 90 preferably are rounded or chamfered and slop toward the channel opening 56 to guide the connector tubular body 34 or the elongated central spline 44a into the channel 52. As a result, the connector 22 slides more smoothly over the end strip upper ends 90 and into the channel 52 as the flexible walls 66 are deflected outwardly by the interference with the connector 22 during the insertion process.

As seen in FIGS. 3, 4, 8, 9 and 10, the distal end portion 74 defines a distal section 92 of the channel that also inhibits unintentional transverse movement of connector 22. For this purpose, the distal channel section 92 has a generally truncated, circular cross-sectional shape that extends through an arc of greater than 180°. The distal channel section 92 has a diameter sized to receive the tubular body 34 of the connector 22. In an exemplifying embodiment, the distal channel section 92 extends through an arc of about 200° about the channel axis c. The channel section 92, in cross-section, thus extends through an arc of a little more than 180° about the channel axis c such that the lateral width of the opening 56 is slightly smaller to the overall diameter of the channel section 92. This allows for the connector 22 to be snapped into the central channel 52.

The distal end portion 74 includes side walls 94 between which the distal channel section 92 is defined. The side walls 92 are substantially identical and extend longitudinally from a point next to the corresponding flexible wall 66 to the distal end of the retainer 30.

Figure 8:
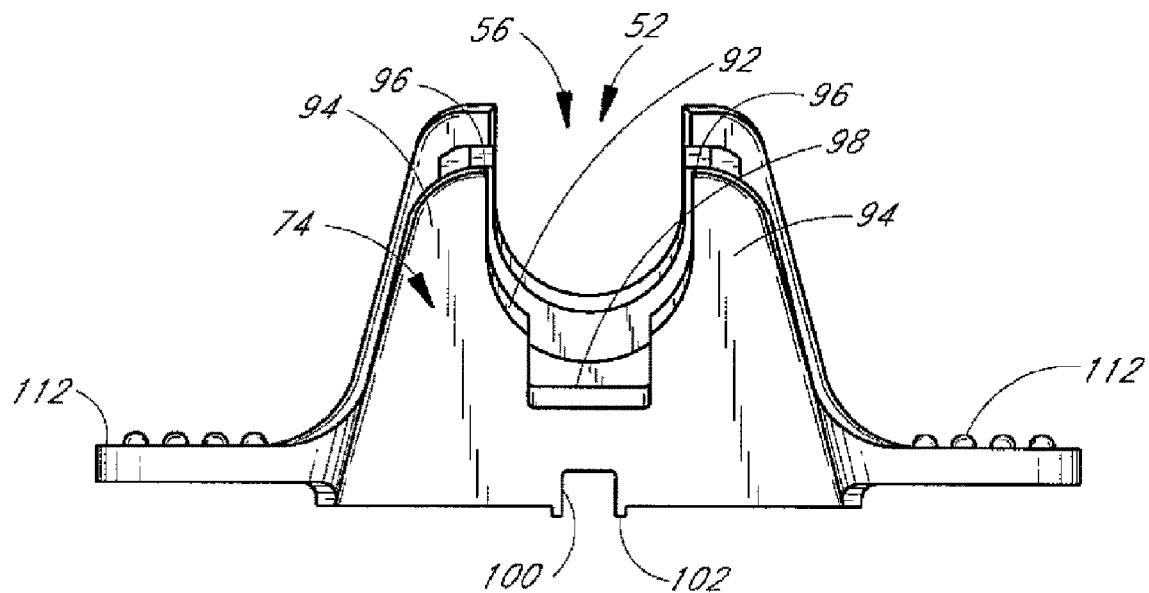
FIG. 8 is an elevational distal end view of the retainer of FIG. 3.

As appreciated from FIGS. 3 and 8, the upper edges 96 of the side walls 94 preferably are rounded or chamfered and slop toward the distal channel section 92 to guide the connector tubular body 34 into the channel 52. As a result, the connector 22 slides more smoothly over the upper edges 96 of the side walls 94 and into the channel 52 as the walls 94 are deflected outwardly by the interference with the connector body 34 during the insertion process.

The walls 94 preferably wrap around a sufficient amount of the connector 22 to inhibit unintentional transverse movement of the connector 22 relative to the retainer 30. As understood from the above description, the upper ends of the walls 94 curve inwardly to narrow the lateral width of the channel opening 56. The extent to which the upper ends can extend inward is limited, however, in order to permit insertion of the connector 22 into the channel 52 through the opening 56. Accordingly, the walls 94 preferably have a length sufficient to produce the desired retention strength to hold the connector 22 in the retainer 30 against an upwardly directed force (or force component). Of course, where the retainer 30 includes one or more additional mechanisms to resist transverse movement of the connector 22 relative to the retainer 30—for example, increased longitudinal lengths of flexible wall end strips 88 or a snap fit connection between the connector 22 and the proximal end portion 72 of the retainer 30—the length of the walls 94 can be reduced.

In a preferred mode, the walls 94 also have a sufficient length to prevent the connector 22 from yawing (i.e., movement side to side in a longitudinal-lateral plane). That is, the length of the walls 94, which interacts with the connector 22, is sufficient so that the distal end portion 74 does not act as a fulcrum. However, while such wall length is preferred, the wall length can be significantly shorter (e.g. interact with the connector at a single longitudinal point) where the connector body 34 is also held near its proximal end by the flexible walls 66 and/or by the proximal end portion 72.

Each wall 94 has a lateral thickness that decreases from the base surface 54 of the retainer 30 to the top of the retainer 30. In addition, as best seen in FIG. 9, the distal channel section 92 is notched along its base. The resulting relief 98 extends transversely from the channel section 92 toward the base surface 54 and longitudinally through the distal end portion 74. In the illustrated embodiment, the relief 98 has a generally rectangular cross-sectional shape. The relief 98 also has a lateral width less than the diameter of the distal channel section 92, and preferably has a lateral width approximately equal to two-thirds the diameter of the distal channel section 92. The decreased lateral thickness of the walls 94 and the decrease transverse thickness of the distal end portion 74 below the channel 52, as a result of the relief 98, provides increased flexibility to permit the walls 94 to deflect elastically outwardly when pressing the connector tubular body 34 into the channel 52.

The retainer 30 also include a notch 100 that extends longitudinally along the base surface 54 and beneath at least the distal channel section 92. In the illustrated embodiment, the notch 100 runs along the entire longitudinal length of the retainer 30. The notch 100 also decreases in traverse height from it proximal end to its distal end following the slope θ of the channel 52. The lateral width of the notch 100 is less than the diameter of the central channel 52. This notch 100 also enhances the flexible nature of the side walls 94.

The side walls 94, however, are substantially more rigid than the flexible walls 66. That is, greater force is required to laterally deflect the side walls 94 of the distal end portion 74 than is required to laterally deflect the flexible walls 66.

Figure 5:
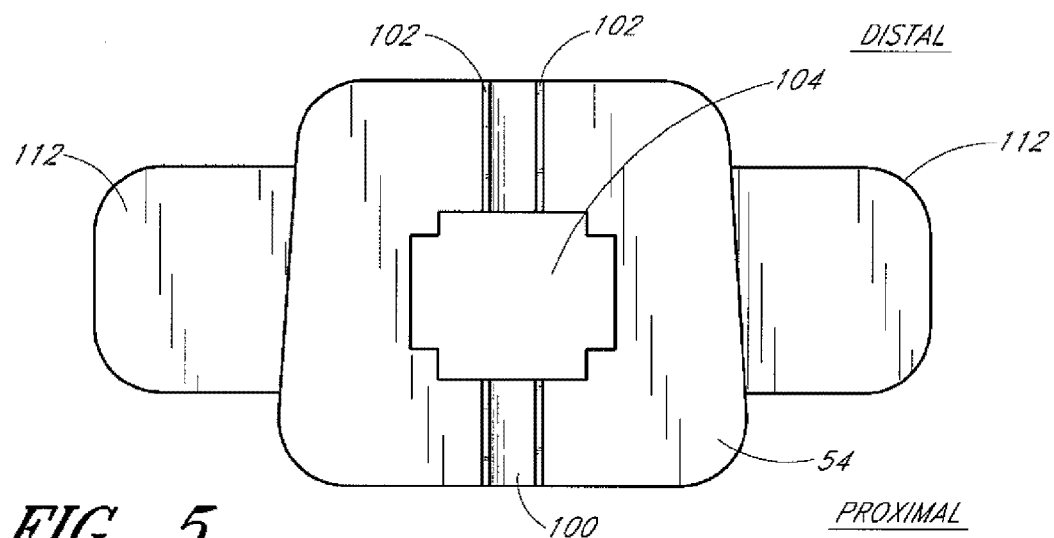
FIG. 5 is a bottom plan view of the retainer of FIG. 3.
Figure 7:
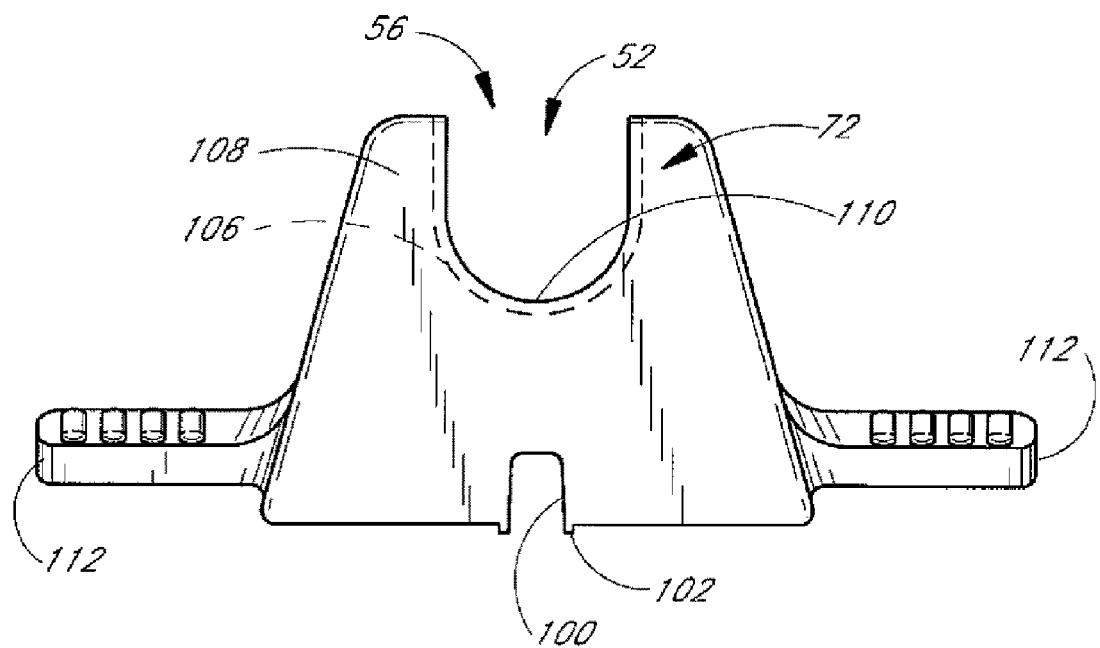
FIG. 7 is an elevational proximal end view of the retainer of FIG. 3.

As seen in FIGS. 5, 7 and 8, a pair of ridges 102 flank the notch 100. Each ridge 102 extends slightly below the base surface 54 to inhibit an influx of adhesive into the notch 100 when the retainer is attached to the anchor pad 28.

The proximal ends of the side walls 94 define at least a portion of the distal-most abutment surface 62. Thus, the distal-most abutment surface 62 constitutes the distal side of each slot 78 between the corresponding side walls 94 and the flexible walls 66. In the illustrated embodiment, the distal-most abutment surface 62 is generally upright.

As seen in FIGS. 4, 5, 9 and 10, a recess 104 is defined in the retainer body 50 at a point between the proximal and distal end portions 72, 74 and between the flexible walls 66, and extends toward the base surface 54 from the channel 52. In the illustrated embodiment, the recess 104 extends between the channel 52 and the base surface 54 in order to reduce the material weight of the retainer 30; however, the recess 104 need only be deep enough to receive one or more of the splines 44 that may extend downward when the connector 22 is inserted into the retainer 30. The recess 104 interrupts the base notch 100, and the channel relief 98 opens into the recess 104 at its proximal end.

The recess 104 is defined by a proximal wall and a distal wall. The distal wall is formed by a proximal end surface of the distal end portion 74 of the retainer 30 and the proximal wall is formed by a distal end surface of the proximal end portion 72 of the retainer 30. Both of these walls lie generally normal to the central axis c of the channel 52 and lie generally in an upright position. The spacing between the walls preferably is as long as the longitudinal length $L_1$ of the central spline 44a. In the illustrated embodiment, the distal wall forms a portion of the distal-most abutment surface 62, and the proximal wall forms a portion of the penult-proximate abutment surface 70. Accordingly, the distal-most abutment surface 62 is formed on the proximal ends of the side walls 94 of the distal end portion 74 and on the distal wall of the recess 104. The penult-proximate abutment surface 70 is formed on the proximal wall of the recess 104.

The proximal end portion 72 defines a proximal section 106 of the channel 52 between the penult-proximate abutment surface 70 and the proximal-most abutment surface 60. The proximal section 106 of the channel 52 generally has a U-shaped cross-section with a radius of curvature at least as large as the radius of the connector tubular body 34. The radius of curvature preferably is larger than the radius of the connector tubular body 34.

The proximal end portion 72 also includes a proximal upstanding wall 108 that extends laterally across the proximal end of the retainer 30. The upstanding wall 108 includes a U-shaped opening 110 that defines the proximal end of the channel 52. The opening 110 has a lateral width that is smaller than the diameter of the connector tubular body 34, but is larger than the diameter of the fluid tube 24. In the illustrated embodiment, the proximal upstanding wall 108 defines the proximal-most abutment surface 60 on its distal side. The proximal-most abutment surface 60 thus, in the illustrated embodiment, lies at the proximal end of the channel proximal section 106.

Both the proximal opening 110 and the proximal section 106 of the channel 52 have generally U-shapes; however, one or both of these channel sections can have a truncated, generally circular shape. In this variation, the opening or the proximal channel section can receive the fluid tube or the proximal end of the connector tubular body, respectively, in a snap fit manner, similar to the distal end portion of the retainer, to inhibit further transverse movement of the connector relative to the retainer. It is preferred, however, that these channel sections do not so engage the connector body or fluid tube in order to ease the insertion process, as described below.

As illustrated in FIG. 3, the retainer 30 includes finger platforms 112 on both sides of the central channel 52. Each finger platform 112 extends laterally from one side of the retainer 30 at a location slightly above the base surface 54. Each finger platform 112 also has a ribbed upper surface to improve frictional contact between a healthcare provider's fingers and the platform 112. The finger platforms 112 are sized and configured to allow a healthcare provider to press the retainer 30 against the skin of the patient while pulling up on the connector 22 when disengaging the connector 22 from the retainer 30.

The combination of the finger platforms 112 and the notch 100 along the base surface 54 beneath the channel 52 makes it easier for the healthcare provider to open the channel 52 to a sufficient degree so as to insert the connector tubular body 34 into the channel 52. This aspect of the anchoring system 20 is not limited to the present retainer. Rather, it can be applied to other types of retainers as well, such as, for example, but without limitation, to those described in U.S. Pat. Nos. 5,702,371, 5,810,781, and 5,827,230, which are hereby incorporated by reference.

The retainer 30 is made of relatively stiff plastic material (e.g. polycarbonate), but is somewhat flexible such that the connector 22 will force the walls 94 of the distal end portion 74, and under some situations the flexible walls 66, outwardly when a healthcare provider presses the connector 22 into the central channel 52 of the retainer 30. When the connector 22 sits in the central channel 52, the upper edges 96 of the walls 94 (and the upper end 90 of the end strips 88) snap inwardly to their original position to securely hold the connector 22 within the retainer 30.

The retainer 30 may be constructed in any of a variety of ways which will be well known to one of skill in the art. For instance, retainer 30 may be integrally molded such as by injection molding or by thermoplasty. The retainer 30 preferably comprises a durably, flexible material, and more preferably comprise a generally inert, non-toxic material. Suitable materials include plastics, polymers, or composites such as polypropylene, polyethylene, polycarbonate, polyvinylchloride, polyurethane, tetrafluoroethylene (e.g. TEFLON7), polytetrafluoroethylene (a.k.a., PTEF), acetal resin (e.g. DELRIN7), chlorotrifluoroethylene (e.g. KEL-F7), acrylonitrile butadiene styrene, styrene butadiene, nylon, olefin, acrylic, polyester, moldable silicon, thermoplastic urethane, thermoplastic elastomers, thermoset plastics and the like. The retainer 30 is preferably formed by injection molding using a polycarbonate, available commercially from GE Plastics (See www.geplastics.com). However, other materials can be used.

Anchor Pad

As is seen in FIG. 1, the anchor pad 28 is a substantially flat piece of material with transversely opposing sides. The lower side of the pad 28 faces toward the skin of the patient, and is preferably covered with an adhesive surface suitable for attaching the anchor pad 28 to the skin of the patient. The entire surface, however, need not be covered. An upper side 120 of the anchor pad 28 faces away from the skin of the patient and supports the retainer 30.

The anchor pad 28 preferably comprises a laminate structure with an upper foam layer (e.g. closed-cell polyethylene foam) and a lower adhesive layer. The lower adhesive layer constitutes the lower surface of the anchor pad 28, i.e., it is coextensive with the upper foam layer. The lower surface desirably is a medical-grade adhesive and can be either diaphoretic or nondiaphoretic, depending upon the particular application. Such foam with an adhesive layer is available commercially from Tyco Adhesives of Norwood, Mass.

A surface of the upper foam layer constitutes the upper surface 120 of the anchor pad 28. The upper surface 120 can be roughened by chemical priming or by corona-treating the foam with a low electric charge. The roughened or porous upper surface 120 can improve the quality of the adhesive joint (which is described below) between the base 54 and the anchor pad 120. In the alternative (not shown), the flexible anchor pad 28 can comprise a medical-grade adhesive lower layer, an inner foam layer and an upper paper or other woven or non-woven cloth layer.

The anchor pad 28 generally has a rectangular shape with rounded corners and elongated extensions that project from the generally rectangular shape. In the illustrated embodiment, these extensions take the form of strips or wings 122 that project from the lateral sides of the anchor pad 28. Each wing 122 preferably has a lateral length that is greater than the circumference of the fluid tube 24 to permit the wing 122 to be wrapped around the tube 24, as illustrated in FIG. 1. The longitudinal width of the wing 122 is sufficient to inhibit the wing 122 from being torn from the anchor pad 28.

In the illustrated embodiment, the wings 122 extend on both lateral sides of the anchor pad 28 to give the healthcare provider the option on which side to form a safety loop. The anchor pad 28, however, can include only one wing or more than two wings. Each wing 122 preferably lies distally of the retainer 30, although the wings 122 can extend from other locations on the anchor pad 28 and/or can have different orientations relative to the retainer 30 (e.g. be skewed relative to the lateral axis) in order to suit particular applications.

This aspect of the anchoring system—an anchor pad including one or more wings to form a safety loop—is not limited to the particular shape of the anchor pad of the illustrated embodiment. It also is not limited to use with the present retainer. Rather, this aspect can be applied in anchoring systems that use other types of retainers, including those noted above, or that employ other anchoring techniques.

The anchor pad 28 also includes a concave section or notch 124, as shown in FIG. 1, that narrows the center of the anchor pad 28 proximate to the retainer 30 and on a distal side of the pad 28. The notch 124 facilitates viewing the indwelling catheter 26, cleansing the insertion site, and placing the anchor pad 28 about the insertion site. This shape also permits the anchor pad 28 to be placed on the patient such that the anchor pad extends beyond the insertion site on the distal side, and away from the insertion site on the proximal other. By aligning the anchor pad 28 and the insertion site of the catheter 26 in this manner, enhanced stability is provided to the catheter 26. This also minimizes the free length of the catheter 26 between the insertion site and the channel 52 of the retainer 30, helping prevent inadvertently catching or pulling on and dislodging of the catheter 26 as the patient moves or as healthcare providers tend the patient.

Another concave section 126 also narrows the center of the anchor pad 28 proximate to the retainer 30 on a proximal side of the pad 28. The concave sections 124, 126 together give the anchor pad 28 greater flexibility at its midsection, thus allowing the anchor pad 28 to sit flat against the skin and follow any surface undulations (e.g. follow the curvature over the patient's knuckles).

The retainer 30 is preferably centered upon the anchor pad 28 about an axis which bifurcates the concave sections 124, 126. Consequently the lateral sides of the anchor pad 28 have more contact area with the skin, both distally and proximally of the retainer 30 in the longitudinal direction, which provides greater stability and adhesion to the skin while still permitting the retainer 30 to be located near the insertion site. Although not illustrated, the anchor pad 28 also can include suture and/or breather holes which are positioned to the sides of the retainer 30.

The retainer base 54 is attached to the upper surface 120 of the anchor pad 28. The bottom surface 54 preferably is secured to the upper surface 120 by a solvent bond adhesive, such as cyanoacrylate or other bonding material. One such adhesive is available commercially as Part No. 4693 from the Minnesota Mining and Manufacturing Company (3M).

A removable paper or plastic release liner (not shown) desirably covers the adhesive lower surface before use. The release liner preferably resists tearing and desirably is divided into a plurality of pieces to ease attachment of the anchor pad 28 to a patient's skin. In the illustrated embodiment, the release liner is split along a centerline of the anchor pad 28 in order to expose only half of the adhesive lower surface at one time. In addition, the release liner is kiss-cut at the base of each wing 122 such that the adjacent half of the adhesive surface can be exposed without removing the portion of the release liner that covers the wing 122.

The length of each release liner piece, as measured in the lateral direction, extends beyond the centerline of the anchor pad 28 and is folded over, or back onto the release liner. This folded over portion defines a pull-tab to facilitate removal of the release liner from the adhesive lower surface. A healthcare worker uses the pull-tab by grasping and pulling on it so that the release liner is separated from the lower surface. The pull-tab eliminates the need to pick at a corner edge or other segment of the release liner in order to separate the release liner from the adhesive layer. The pull-tab of course can be designed in a variety of configurations. In addition, the pull-tab need not be located along a centerline of the anchor pad 28; rather, the pull-tab can be located along any line of the anchor pad 28 in order to ease the application of the anchor pad 28 onto the patient's skin at a specific site. For example, an area of a patient's skin with an abrupt bend, such as at a joint, may require that the pull-tab be aligned toward one of the lateral sides of the anchor pad 28 rather than along the centerline.

Method of Use

Figure 11A:
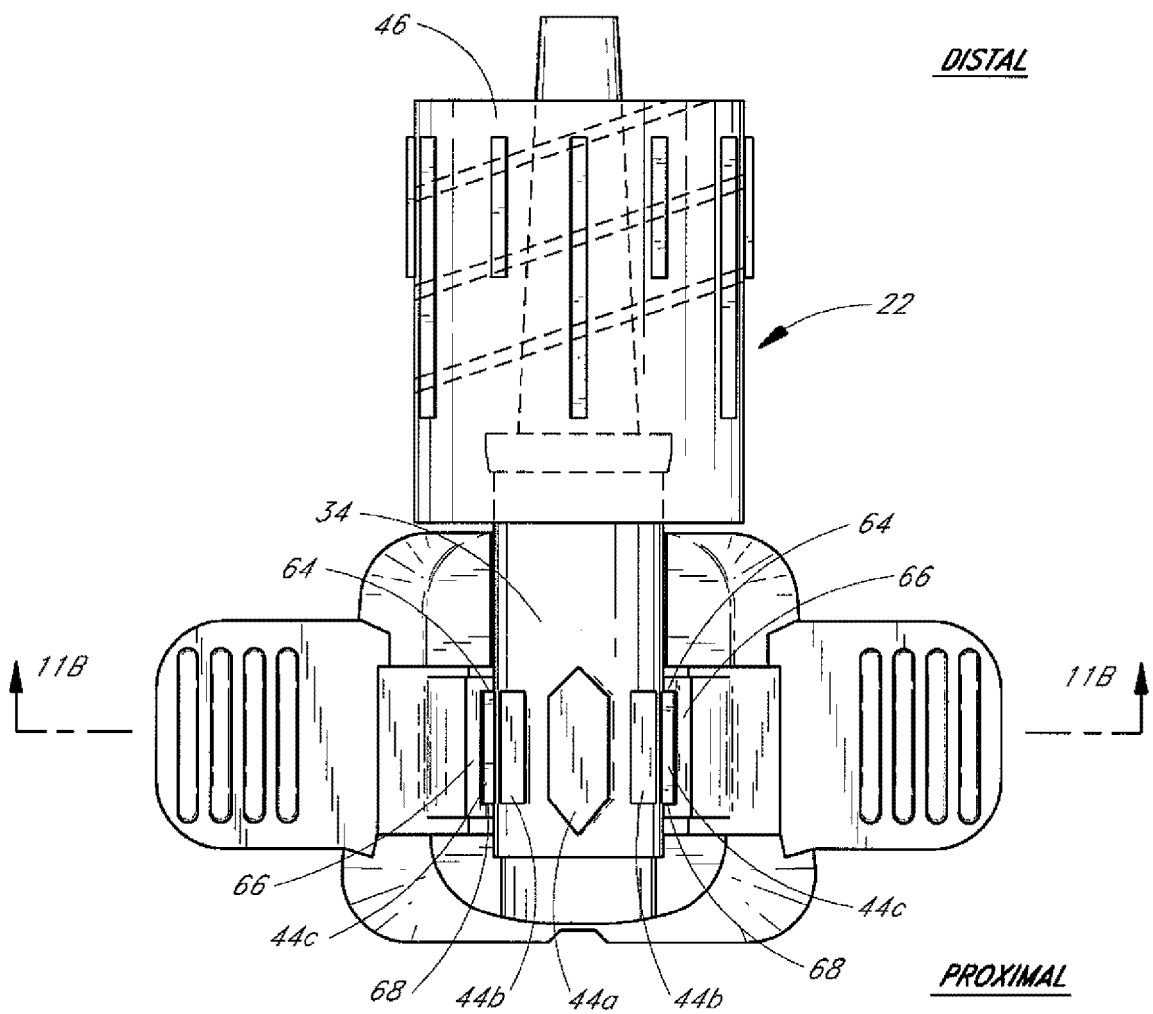
FIG. 11A is a top plan view of the catheterization system of FIG. 1 with the connector inserted with splines orientated upward (the tubing, which is illustrated in FIG. 1 as extending from the connector, has been omitted to simplify the drawing)
Figure 11B:
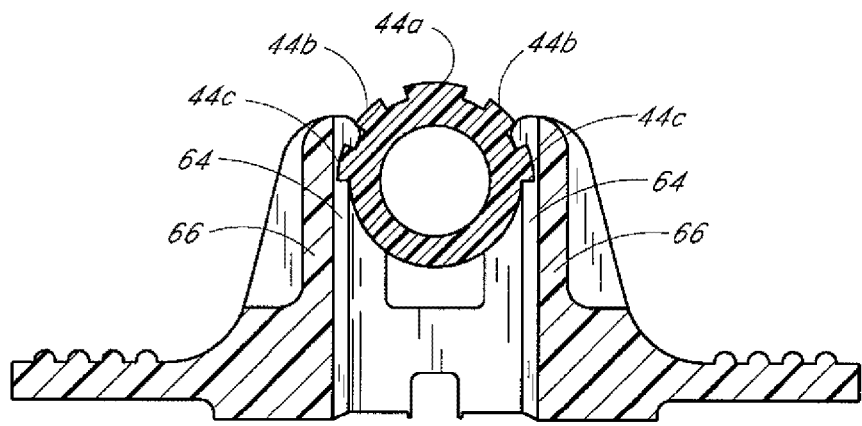
FIG. 11B is a cross-sectional view of the catheterization system of FIG. 11A, taken along the 11B-11B line.
Figure 11C:
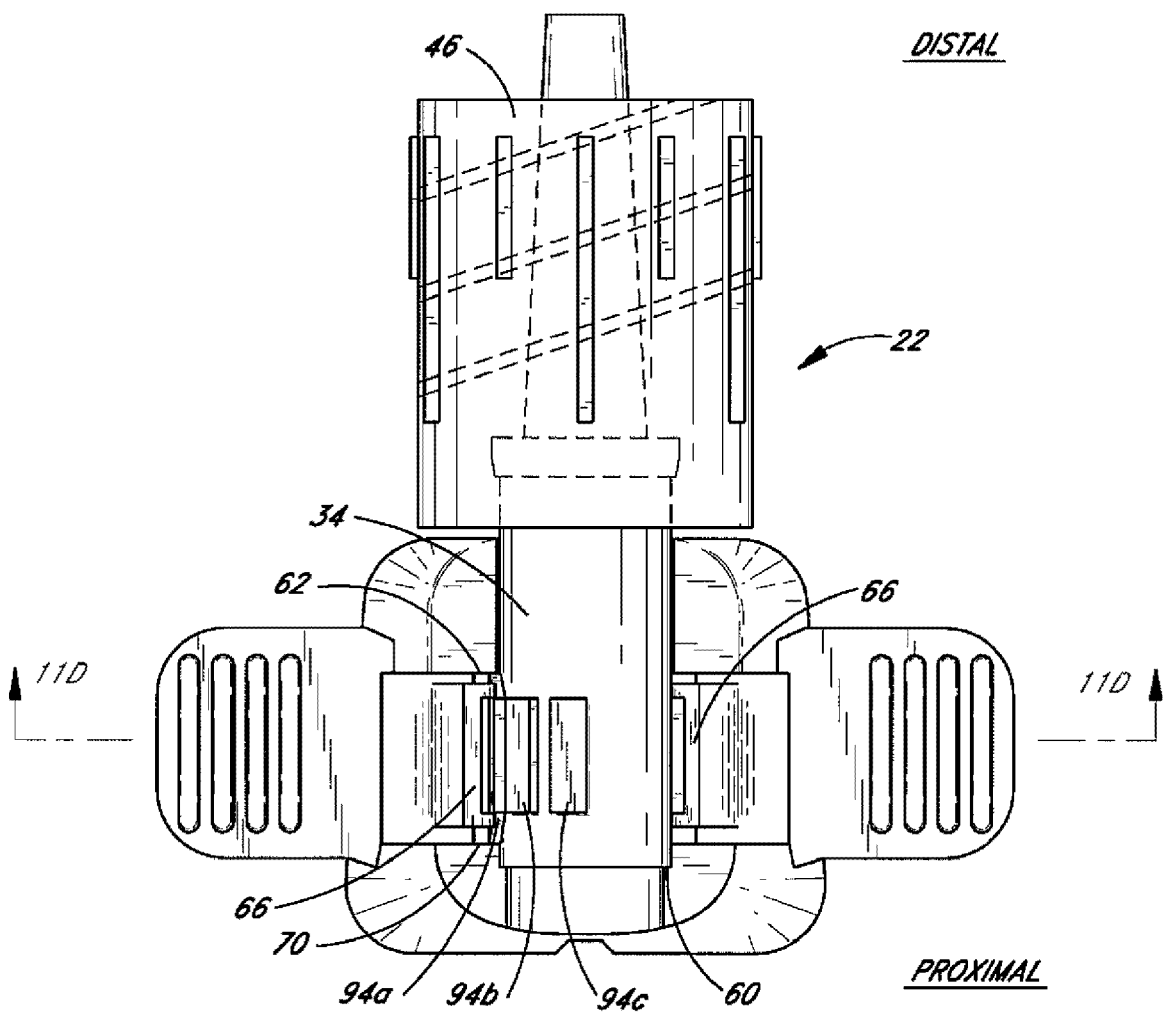
FIG. 11C is a top plan view of the catheterization system of FIG. 1 with the connector inserted with the splines rotated 90° from their position in FIG. 11A (the tubing also has been omitted in this drawing)
Figure 11D:
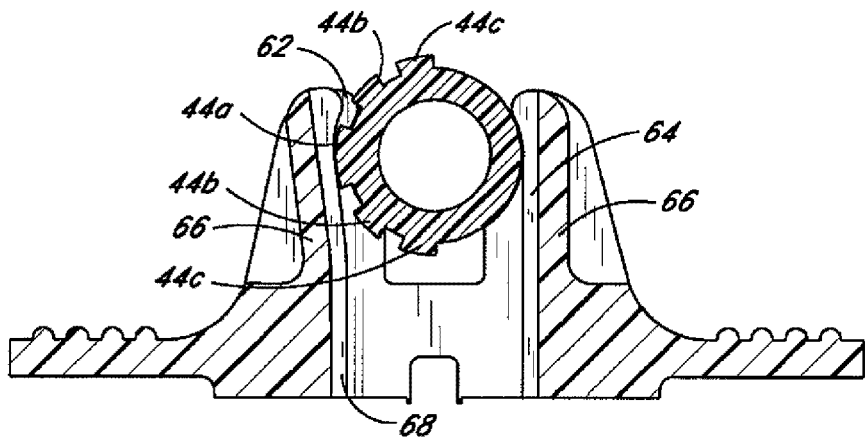
FIG. 11D is a cross-sectional view of the catheterization system of FIG. 11C, taken along the 11D-11D line.
Figure 11E:
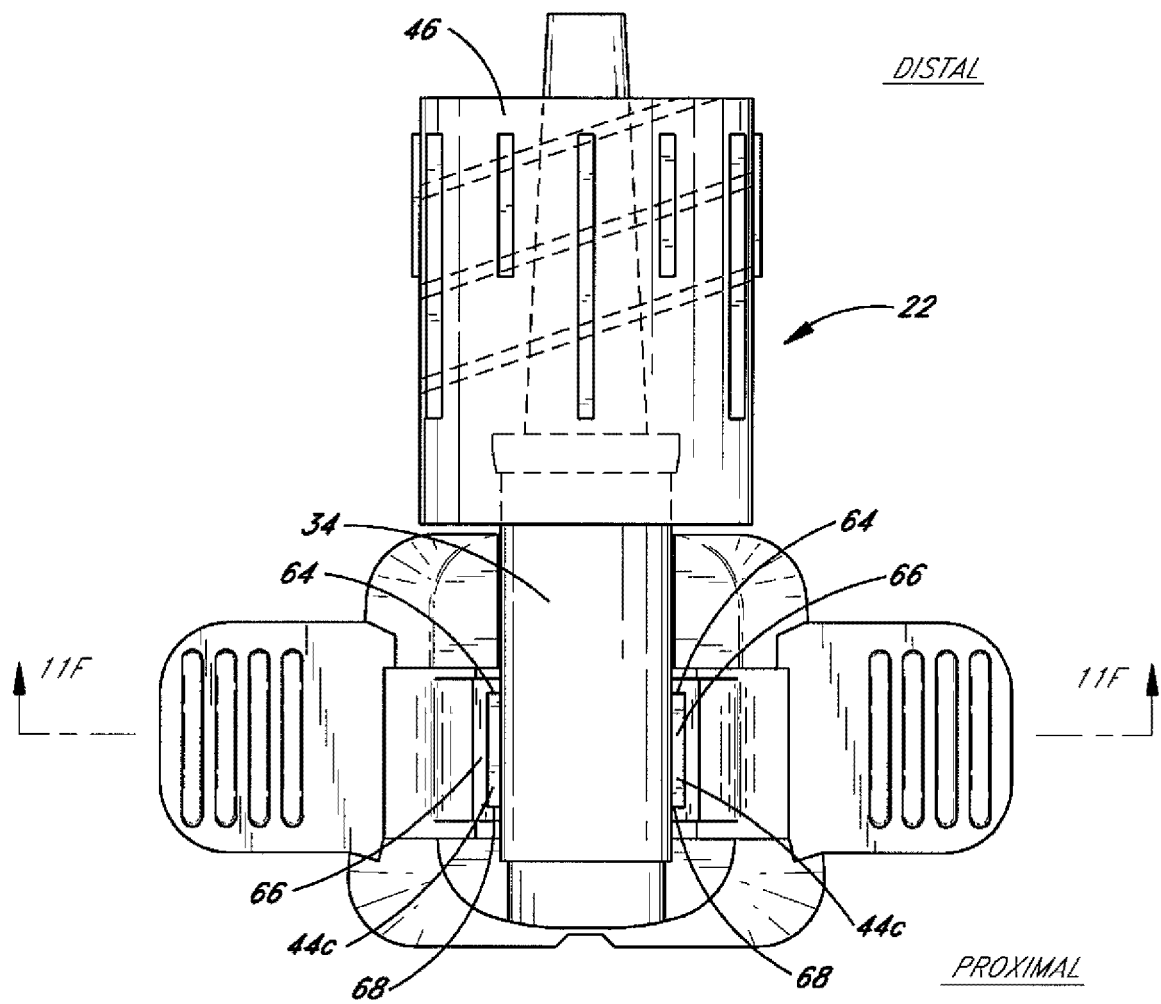
FIG. 11E is a top plan view of the catheterization system of FIG. 1, with the connector inserted with the splines rotated 180° from their position in FIG. 11A (the tubing again has been omitted from this drawing)
Figure 11F:
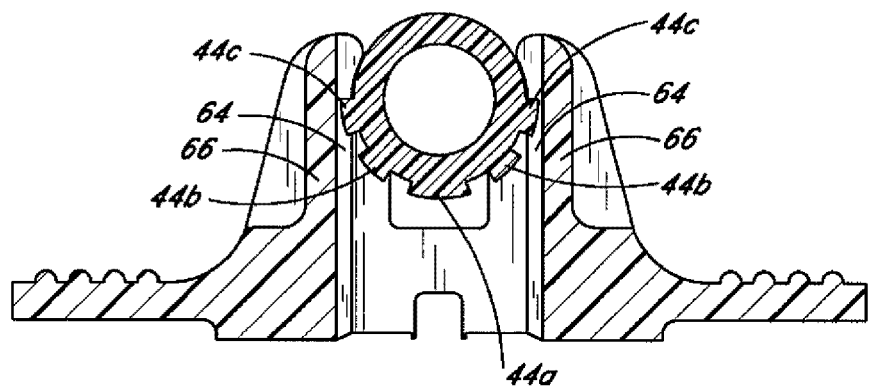
FIG. 11F is a cross-sectional view of the catheterization system of FIG. 11E, taken along the 11F-11F line.
Figure 12:
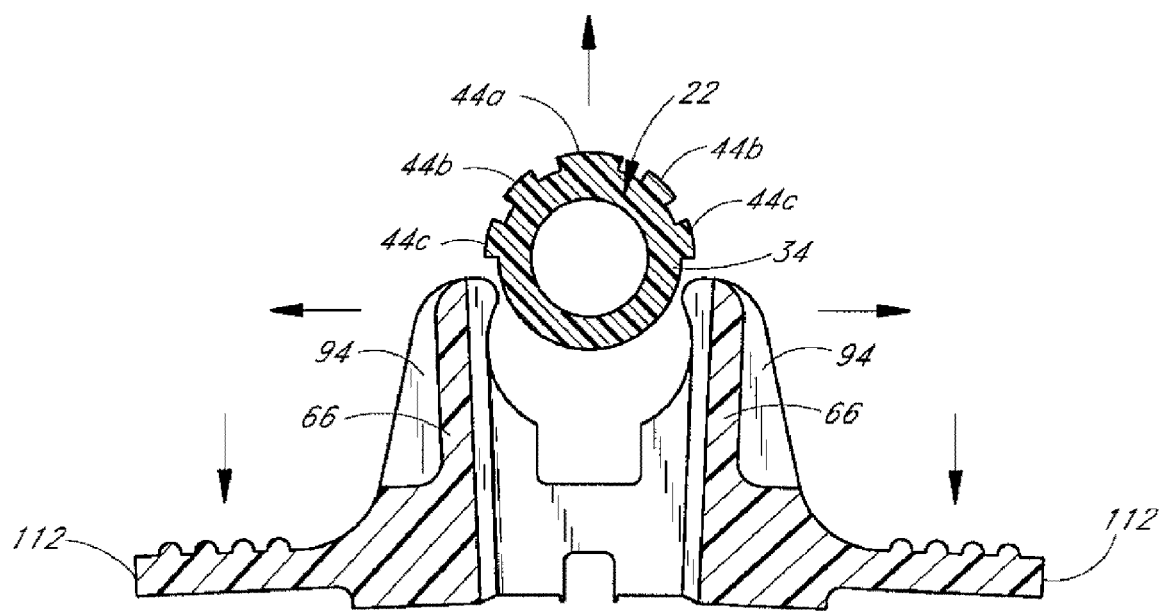
FIG. 12 is a cross-sectional view of the retainer of FIG. 4, taken along the 9-9 line, with the catheter connector being withdrawn.

The following discussion of the method of use will be with reference to FIGS. 1 and 11-12, and will be in the context of intravenous catheterization. As the following discussion will illustrate, however, it is understood that the anchoring system 20 can be used in other catheterization procedures as well. The discussion of the method of use is intended to augment the above description of the invention, and, thus, should be read together.

A healthcare provider typically begins the catheterization process by positioning the catheter 26 at a desired location above a vein. The healthcare provider introduces a needle or other stylus through a cannula portion of the catheter 26 and into the skin of the patient at a desired angle of incident. For intravenous use, the catheter 26 commonly has an incident angle of approximately 7°. The healthcare provider then inserts the cannula of the catheter 26 into the patient and withdraws the needle or stylus. Part of the catheter 26 remains exposed above the skin. The healthcare provider inserts the proximal end of the connector 22 into the catheter hub 32. The healthcare provider then securely attaches the connector 22 to the catheter 26 by engaging the spin nut 46 with the catheter hub 32 in a known manner.

The healthcare provider positions the retainer 30 below the connector 22 and inserts a portion of the fluid tube 24 through the proximal opening 110. At this point, the axis of the connector 22 is skewed relative to the axis c of the retainer channel 52. The healthcare provider pulls the fluid tube 24 proximally (or conversely slides the retainer distally) until the proximal end 38 of the connector tubular body 34 contacts the proximal-most abutment surface 60. This act registers the longitudinal position of the connector 22 with the retainer 30 to align the connector 22 above the retainer 30. So positioned, the longitudinal midpoint of the splines 44 on the connector 22 is aligned with the longitudinal midpoint of the flexible walls 66 of the retainer 30 and with the longitudinal midpoint between the penult-proximate and distal-most abutment surfaces 70, 62. The healthcare provider then presses the connector 22 into the central channel 52 of the retainer 30. In doing so, the connector 22 is pressed between the distal end portion walls 94 of the retainer 30. As the healthcare provider presses the connector 22 into the retainer 30, the splines 44 are generally guided into either the space between the intermediate proximal and distal and abutment surfaces 64, 68 or the space between the penult-proximate abutment surface 70 and the distal-most abutment surface 62.

As mentioned above, the opening 56 of the channel 52 has a smaller width measured in the lateral direction than the diameter of the connector tubular body 34. The distal end portion walls 94 thus deflect outwardly in a lateral direction. Once the tubular body 34 of the connector 22 rests within the central channel 52 of the retainer 30, the lateral walls 94 spring back to snap the connector 22 in place. The walls 94 of the retainer 30 thus prevent unintentional transverse and lateral movement of the connector 22. As noted above, the flexible walls 66 also deflect and snap around the tubular body 34 during the insertion process.

Once the connector 22 is secured in the retainer 30, the healthcare provider removes the paper backing which initially cover the adhesive bottom surface of the anchor pad 28, and attaches the pad 28 to the patient's skin proximate to the indwelling catheter 26. Specifically, the healthcare provider grips the one of the two backing tabs. The healthcare provider then pulls on the tab and peels the backing off one side of the bottom adhesive layer. The healthcare provider positions the anchor pad 28 over the placement site and places the exposed bottom layer against the patient's skin to adhere the anchor pad 28 to the patient. Light pressure over the upper layer 120 assures good adhesion between the anchor pad 28 and the patient's skin. The anchor pad 28, due to its flexibility, conforms to the contours of the topical surface to which the anchor pad 28 adhere.

The healthcare provider repeats this procedure for the other side of the bottom surface of the anchor pad 28. Alternatively, the healthcare provider may completely remove the backing from the pad 28 before attaching the pad 28 to the patient's skin. Additionally, the anchor pad 28 can be attached to the patient before the connector 22 is inserted into the retainer 30.

Either before or after the anchor pad 28 is attached to the patient's skin, the healthcare provider secures a portion of the fluid tube 24 to the anchor pad 28 using one of the elongated wings 122 to form a safety loop. The healthcare provider removes the backing under the wing 122 on what ever side of the anchor pad 28 he or she elects to attach the tube 24, and wraps the wing 122 around the tube 24 with the adhesive layer contacting the tube 24. In so doing, the distal end of the wing 122 is placed on the tube 24, and the tube 24 is rolled toward the pad 28 to roll the tube 24 and the distal end of the wing 122 under the balance of the wing 122. This process continues until the wing 122 extends about a substantial portion of the tube circumference. The healthcare provider preferably wraps the wing 122 around the entire circumference.

The wing 122 on the other side of the anchor pad 28 can be attached to the patient's skin by removing the backing and applying light pressure. This step can be done when applying the rest of the anchor pad 28 to the patient or after. Alternatively, the healthcare provider can cut the unused strip off the pad 28 if so desired. In some instances, the healthcare provider may elect not to form a safety loop in this manner. Additionally, the anchoring system can include a clip, such as disclosed in U.S. Pat. No. 5,827,230, to form the safety loop.

FIGS. 11A-F illustrate how the retainer 30 prevents the longitudinal movement of the connector 22 in both the proximal and distal directions once the connector 22 is positioned within the channel 52, irrespective of the position of the splines 44 when the connector 22 is inserted into the retainer 30. In FIGS. 11A and 11B, the connector 22 is situated such that the elongated spline 44a faces away from the retainer base surface 54. When the connector 22 is situated as such and the healthcare provider presses the connector 22 into the retainer 30, the diametrically opposed splines 44c slide into the recesses or spaces between the intermediate proximal and distal abutment surfaces 68, 64. Once inserted fully, these abutment surfaces 68, 64 restrain the diametrically opposed splines 44c and thus inhibit longitudinal movement of the connector 22 in both the proximal and distal directions.

In FIGS. 11C and 11D, the connector 22 is situated such that the elongated spline 44a is rotated about 90° from its position in FIG. 11A. As the connector 22 is inserted as situated, the elongated spline 44a contacts and pushes laterally and outwardly one of the flexible walls 66, and accordingly, the intermediate proximal and distal abutment surfaces 64, 68 are also moved laterally. The longitudinal ends of the elongated spline 44a fall between the penult-proximate abutment surface 70 and distal-most abutment surface 62. These abutment surfaces 70, 62 longitudinally restrain the elongated spline 44a and thus inhibit the longitudinal movement of the connector 22 relative to the retainer 30. In particular, the distal-most abutment surface 62, against which the distal end of the elongated spline 44a acts when moved distally, inhibits longitudinal movement of the connector 22 in the distal direction. The penult-proximate abutment surface 70, against which the proximal end of the elongated spline 44a acts when moved proximally, inhibits proximal movement of the connector 22 in the proximal direction.

In FIGS. 11E and 11F, the connector 22 is situated such that the elongated spline 44a is rotated about 90° from its position in FIG. 11C and about 180° from its position in FIG. 11A. In this case, the diametrically opposed splines 44c are restrained as they were in FIG. 11A, thus inhibiting the longitudinal movement of the connector 22. In this position, the elongated spline 44a is situated within the recess 104 below the channel 52. The distal-most abutment surface 62 and the intermediate distal abutment surface 64, against which the distal ends of the splines 44a, 44c respectively act when moved distally, together inhibits longitudinal movement of the connector 22 in the distal direction. The penult-proximate abutment surface 70 and the intermediate proximal abutment surface 68, against which the proximal ends of the splines 44a, 44c respectively act when moved proximally, together inhibits proximal movement of the connector 22 in the proximal direction.

The preceding scenarios merely illustrate the functioning of the retainer 30. As will be readily apparent to one skilled in the art, no matter what position the connector 22 and its splines 44 are in, at least one of the splines 44 is retained by one or more of the retainer's abutment surfaces and thus longitudinal movement of the connector is inhibited. For instance, at an intermediate position between the positions illustrated in FIGS. 11A and 11B and in FIGS. 11C and 11D, at least one of the intermediate splines 44b is longitudinally restrained between the intermediate proximal and distal abutment surfaces 68, 64. In this manner, longitudinal movement of the connector 22 in both the proximal and distal directions is restrained relative to the retainer 30.

Additionally, the proximal-most abutment surface 60 arrests longitudinal movement of the connector 22 in the proximal direction irrespective of the positions of the connector splines 44 when the connector 22 is inserted into the retainer 30. The proximal end 38 of the connector 22 abuts or contacts the proximal-most abutment surface 60 of the retainer 30 in every rotational position of the connector 22. Accordingly, the proximal-most abutment surface 60 also inhibits proximal movement of the connector 22 along in the longitudinal direction.

As noted above, a variation of the retainer can eliminate the penult-proximal and the intermediate proximate abutments surfaces 70, 68 when the retainer includes the proximal-most abutment surface 60 to inhibit proximal movement. In another variation of the retainer, the proximal-most abutment surface 60 can be omitted when one or both of the penult-proximate abutment surface 70 and the intermediate proximate abutment surface 68 are arranged to arrest proximal longitudinal movement of the connector 22 relative to the retainer 30.

FIG. 12 illustrates the removal of the connector 22 from the retainer 30. The healthcare provider places to two fingers on the finger platforms 112 and presses down slightly. The force from the pressure on the finger platforms 112 causes the upper ends of side walls 94 and the flexible walls 66 to spread apart laterally. Consequently, the upper opening 56 of the retainer channel 52 opens to a size slightly greater than the diameter of the connector 22. The healthcare provider then lifts the connector 22 out of the central channel 52.

As understood from the above description of the catheter anchoring system embodiment shown in FIG. 1, the catheter anchoring system 20 cooperates with a luer lock connector 22 that securely connects a tube 24 (e.g., a fluid supply line) to an indwelling catheter 26. The cooperation between abutment surfaces on the retainer 30 (FIGS. 3-10) and the connector 22 maintains the catheter 26 in the desired indwelling position. These abutment surfaces can include, for example, a proximal-most abutment surface 60, a distal-most abutment surface 62 and one more intermediate surfaces 64, 68. The intermediate surfaces 64, 68 lie between the proximal- and distal-most abutment surfaces 60, 62 and are defined on a flexible wall 66. The proximal- and distal-most abutment surfaces 60, 62 preferably are separated by a distance that is generally equal to the longitudinal length $L_3$ between the proximal end 26 of the connector tubular body 34 and a distal tip of the central spline 44a.

The retainer 30 (FIG. 3-10) can further include a penult-proximate abutment surface 70 disposed between the proximal-most abutment surface 60 and the intermediate proximal abutment surface 68. The penult-proximate abutment surface 70 lies generally normal to the central axis C of the channel 52 and is distanced from the distal-most abutment 62 surface by the longitudinal length $L_1$ of the central spline 44a.

As described in connection with the embodiment shown in FIGS. 3-10, the flexible wall 66 can include two intermediate abutment surfaces: an intermediate proximal abutment surface 68 and an intermediate distal abutment surface 64. In the embodiment shown in FIGS. 3-10, these abutment surfaces 64, 68 face each other and are spaced apart by a distance that is generally equal to the longitudinal length $L_2$ of the intermediate and outer splines 44b, 44c of the luer lock connector 22.

Additional Embodiments

A variation of the retainer design is described below in connection with FIGS. 13-21 that omits the abutment surfaces 64, 68 from the flexible wall 66 of the retainer. In the absence of the abutment surfaces 64, 68, other abutment surfaces, for example, the proximal-most abutment surface 60, the penult-proximate abutment surface 70, and/or the distal-most abutment surface 62, cooperate with contact points or surfaces on the luer lock connector 22 to arrest movement in the longitudinal direction. Depending on what contact points or surfaces are provided on the luer lock connector 22, the proximal-most abutment surface 60, the penult-proximate abutment surface 70, the distal-most abutment surface 62, and/or other abutments on the retainer 300 will generally abut against one or more of the contact points or surfaces (a gap between the abutment and the contact points can occur in some applications). Additional or redundant abutment points or surfaces may still be provided.

Figure 13:
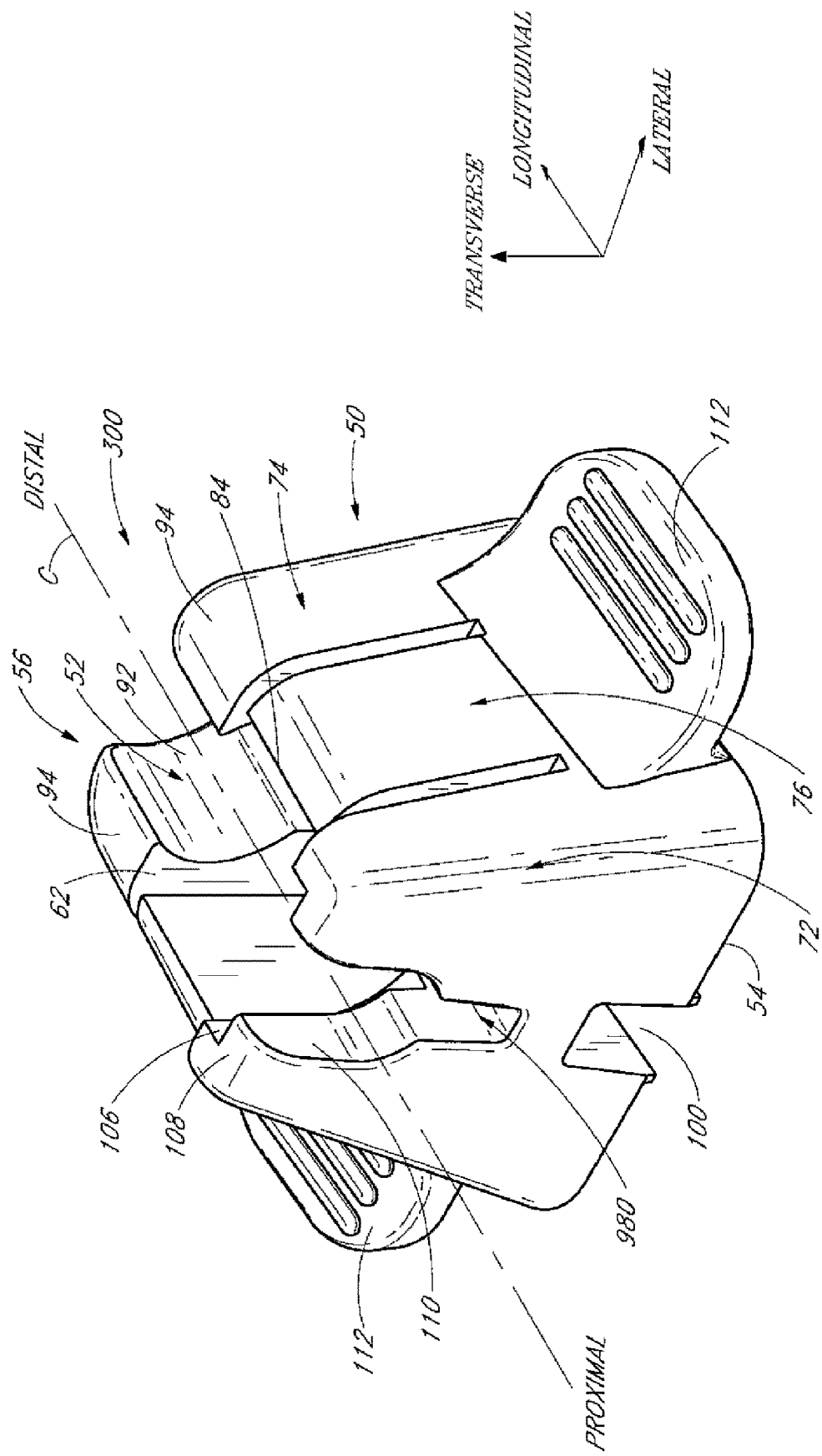
FIG. 13 is a perspective view of a retainer that can be used with the catheterization system of FIG. 1, which is configured in accordance with another preferred embodiment of the present invention.
Figure 14:
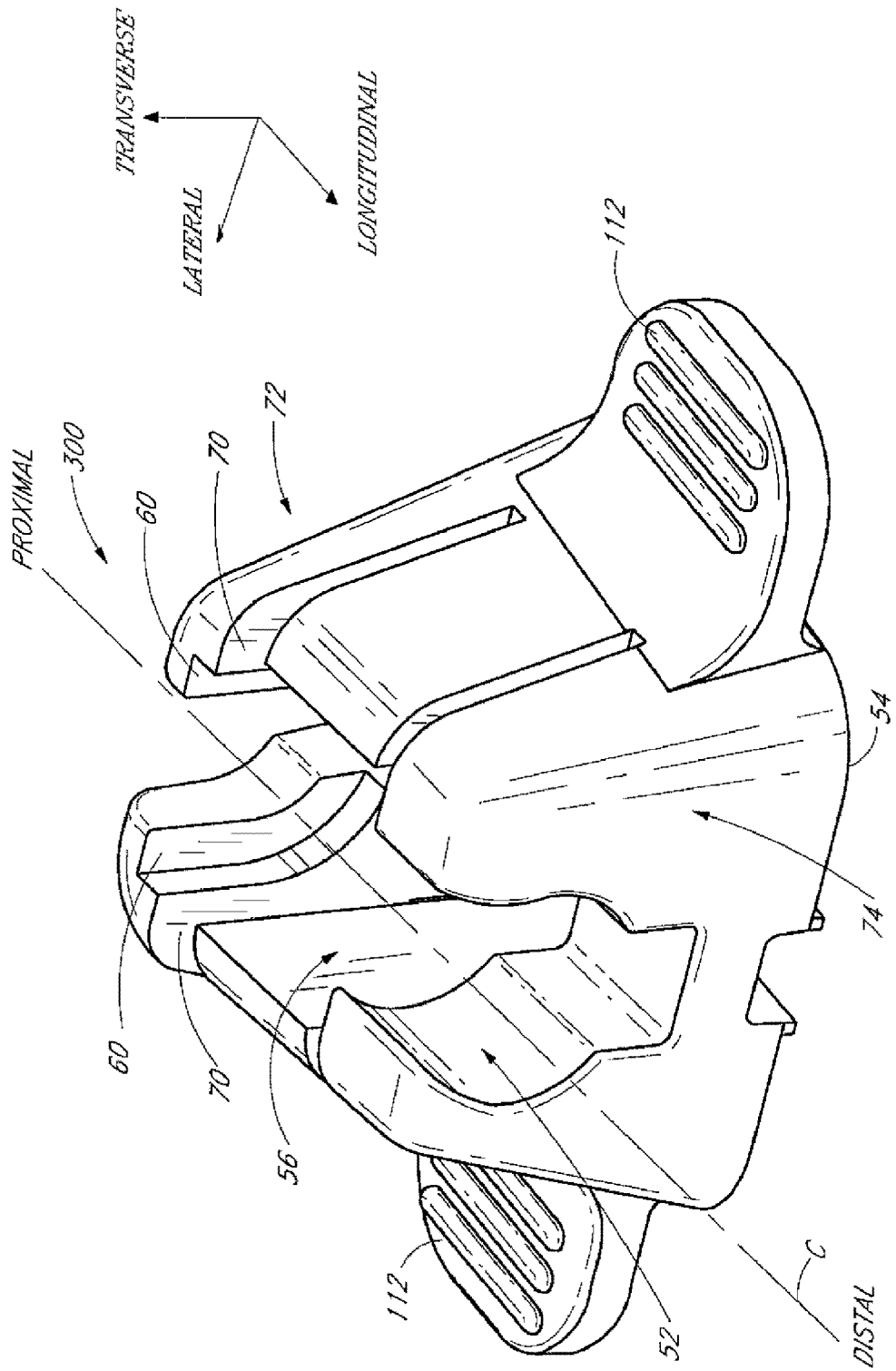
FIG. 14 is a second perspective view of the retainer illustrated in FIG. 13 as viewed from a higher angle.

A retainer 300 which omits the abutment surfaces 64, 68 is illustrated in FIGS. 13 and 14. The retainer 300 is similar to the retainer 30 in the catheter anchoring system 20 shown in FIG. 1 above. Only the retainer 300 of this embodiment differs from the above-described catheter anchoring system 20. Accordingly, the above description of the catheter anchoring system applies equally to the embodiment of FIGS. 13-21, unless otherwise indicated.

Figure 22A:
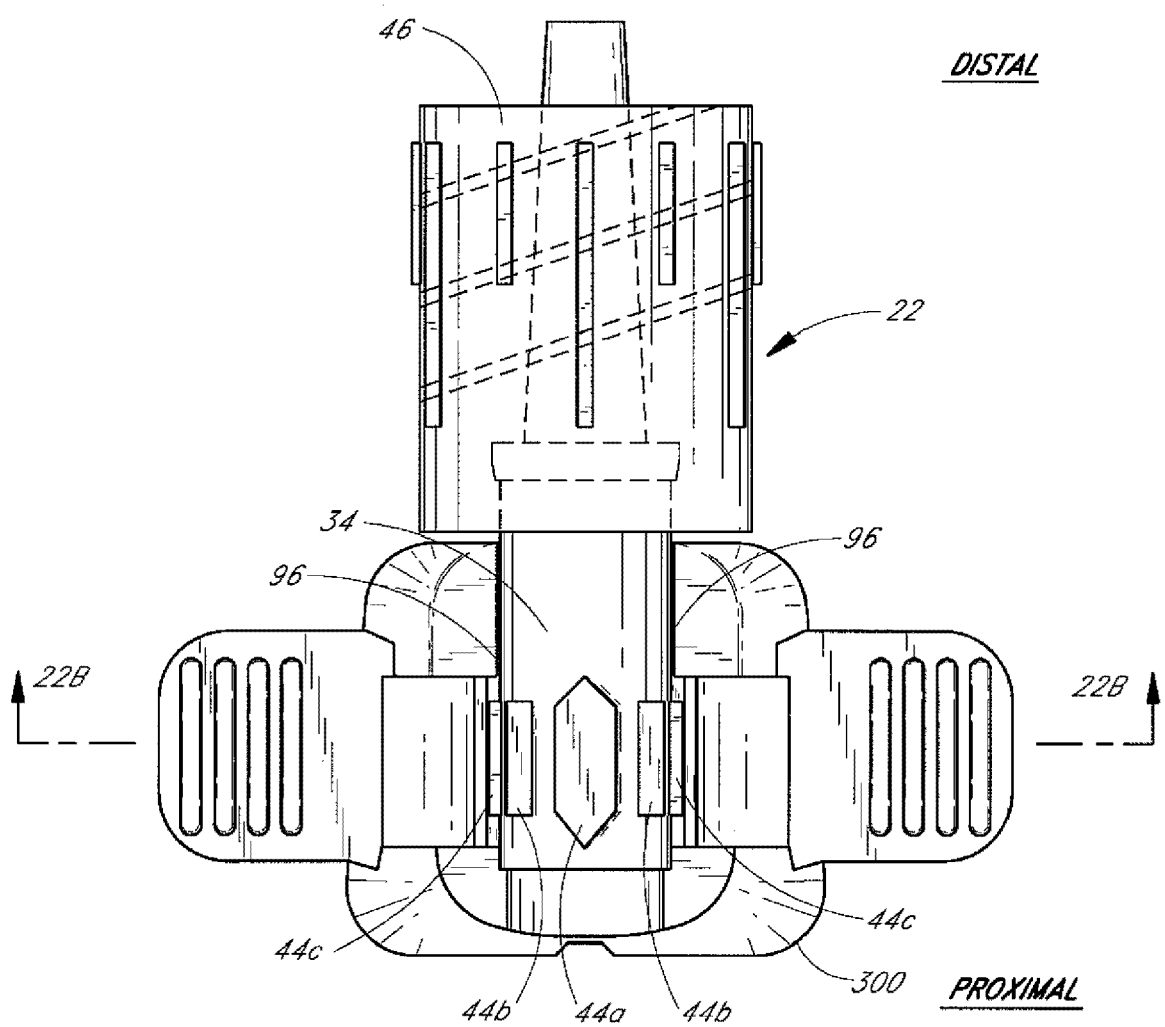
FIG. 22A is a top plan view of a catheterization system including the retainer shown in FIG. 13 with the connector inserted with splines orientated upward (the tubing, which is illustrated in FIG. 1 as extending from the connector, has been omitted to simplify the drawing)

In one form, the retainer 300 is designed to secure a luer lock connector 22 between the penult-proximate abutment surface 70 and the distal-most abutment surface 62 on the retainer 300 as shown in FIG. 22A. In this embodiment, the abutment surfaces 70, 62 extend laterally from the central channel 52. Each abutment surface 70, 62 lies generally normal to the central axis C of the channel 52.

The retainer 300 has a body 50 that defines a central channel 52 disposed above a base surface 54. The channel 50 extends about a central, longitudinally extending axis C and has an opening 56 that faces away from the base surface 54. The proximal and distal ends of the channel 52 also open through the ends of the retainer body 50. At least a portion of the channel 52 has a lateral width that is smaller than the diameter of the connector tubular body 34.

Figure 17:
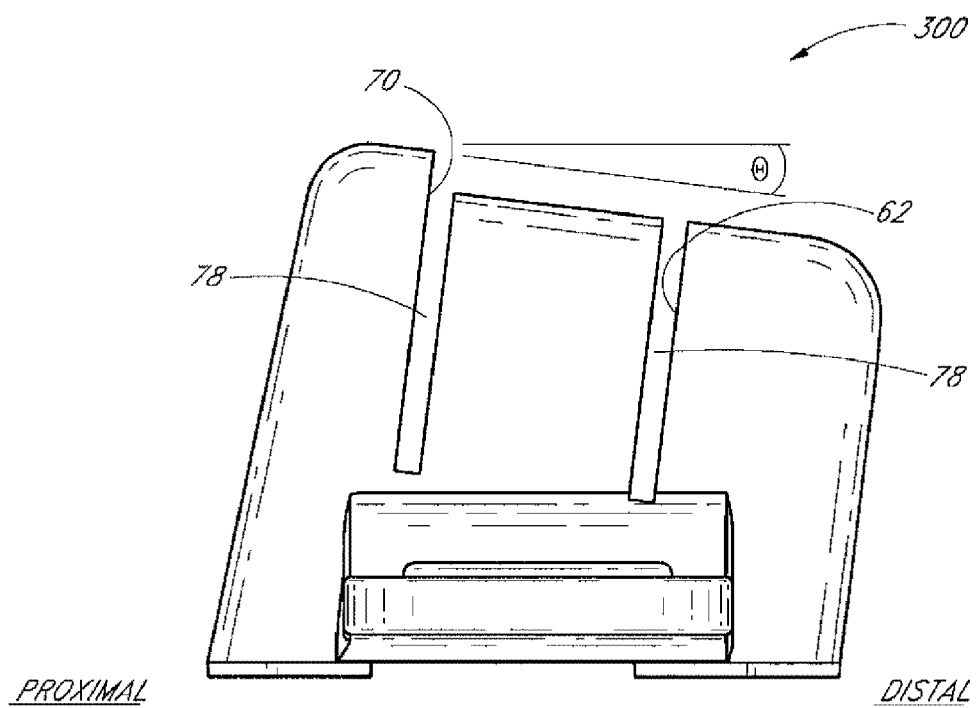
FIG. 17 is an elevational side view of the retainer of FIG. 13.

FIG. 17 illustrates that the channel axis C is desirably skewed relative to a base surface 54 of the retainer 300. An incident angle θ defined between the base surface 54 and the channel axis C preferably is less than 45°. More preferably, the incident angle θ ranges between 5° and 30°. In an exemplifying embodiment for intravenous use, the angle θ preferably equals approximately 7°. In another exemplifying embodiment for arterial use, the incident angle θ preferably equals about 22°.

Figure 15:
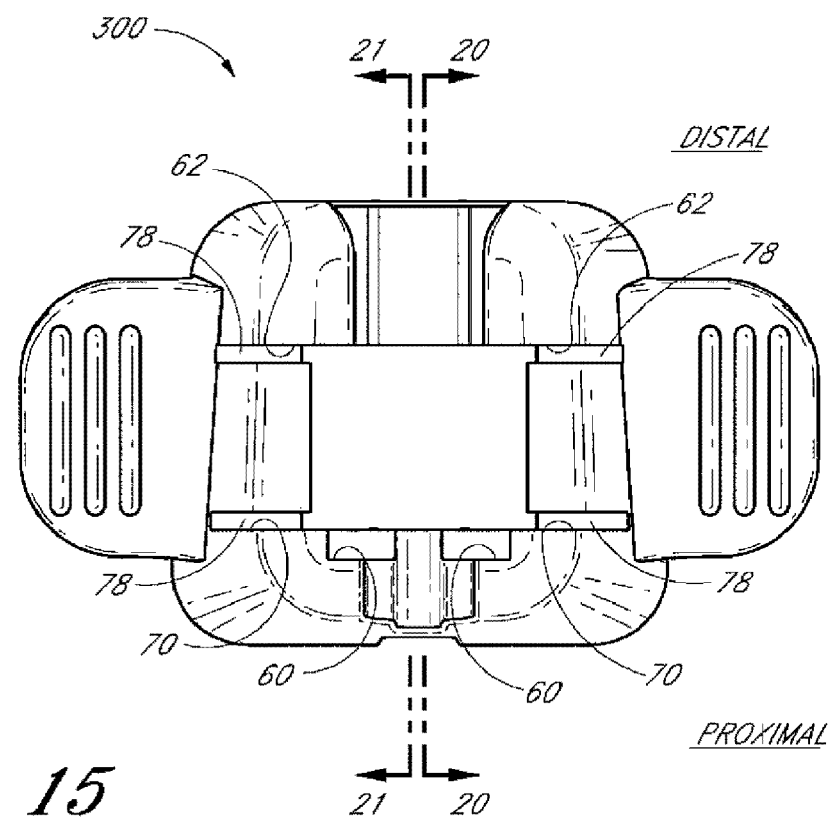
FIG. 15 is a top plan view of the retainer of FIG. 13.

As best seen in FIGS. 13-15, the retainer 300 also includes a plurality of abutment surfaces the extends laterally from the channel 52. Each abutment surface lies generally normal to the central axis C of the channel 52. These abutment surfaces include a proximal-most abutment surface 60 and a distal-most abutment surface 62. The proximal- and distal-most abutment surfaces 60, 62 preferably are separated by a distance that is generally equal to the longitudinal length $L_3$ between the proximal end 26 of the connector tubular body 34 and a distal tip of the central spline 44a.

The illustrated embodiment of the retainer 300, as noted above, includes the additional penult-proximate abutment surface 70 disposed between the proximal-most abutment surface 60 and the distal-most abutment 62 surface. The penult-proximate abutment surface 70 lies generally normal to the central axis C of the channel 52 and is distanced from the distal-most abutment 62 surface by the longitudinal length $L_1$ of the central spline 44a.

As seen in FIGS. 13 and 14, the retainer body 50 includes proximal and distal end portions 72, 74 and an intermediate portion 76. The channel 52 extends through these portions 72, 74, 76 and is open at each of its ends through end walls of the proximal and distal end portions 72, 74.

With reference to FIGS. 13-15 and 17, the intermediate portion 76 is formed by a pair of flexible walls 66 between which the channel 52 passes. Transversely extending slots 78 separate each flexible wall 66 from the adjacent proximal and distal end portions 72, 74. Each flexible wall 66 has a generally flat, upstanding surface 86.

As seen in FIGS. 13-15, the distal end portion 74 defines a distal section 92 of the channel that also inhibits unintentional transverse movement of connector 22. For this purpose, the distal channel section 92 has a generally truncated, circular cross-sectional shape that extends through an arc of greater than 180°. The distal channel section 92 has a diameter sized to receive the tubular body 34 of the connector 22. In an exemplifying embodiment, the distal channel section 92 extends through an arc of about 200° about the channel axis c. The channel section 92, in cross-section, thus extends through an arc of a little more than 180° about the channel axis c such that the lateral width of the opening 56 is slightly smaller to the overall diameter of the channel section 92. This allows for the connector 22 to be snapped into the central channel 52.

The distal end portion 74 includes side walls 94 between which the distal channel section 92 is defined. The side walls 92 are substantially identical and extend longitudinally from a point next to the corresponding flexible wall 66 to the distal end of the retainer 300.

Figure 19:
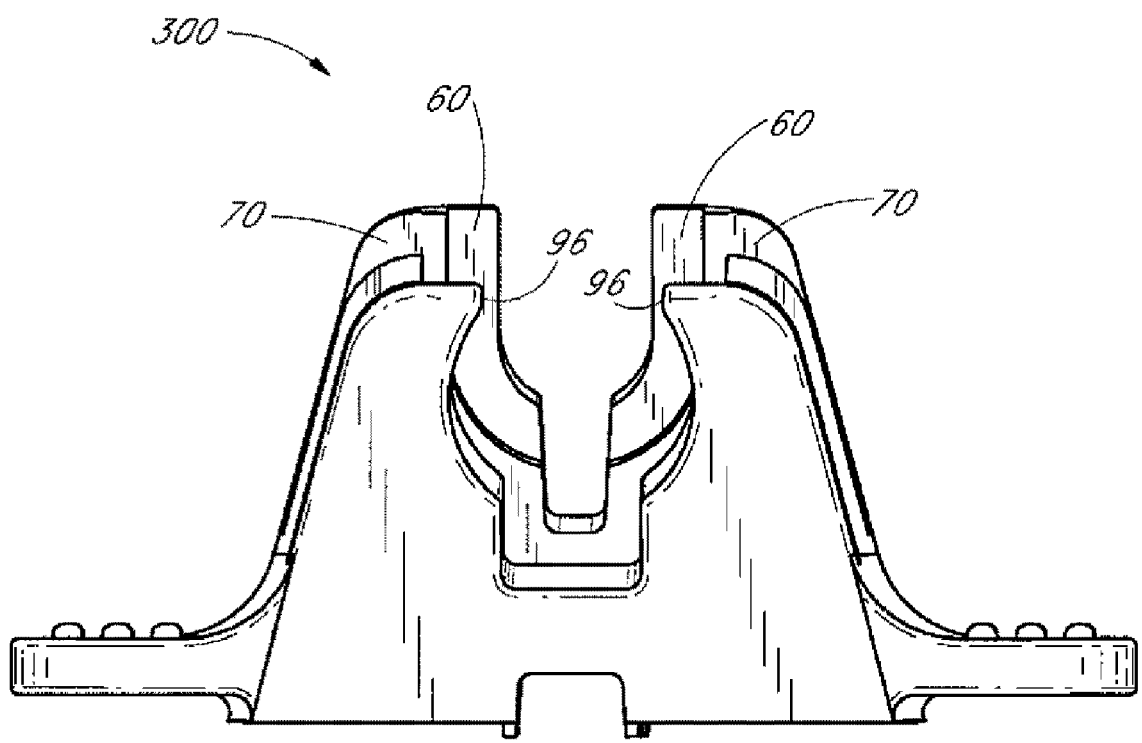
FIG. 19 is an elevational distal end view of the retainer of FIG. 13.
Figure 20:
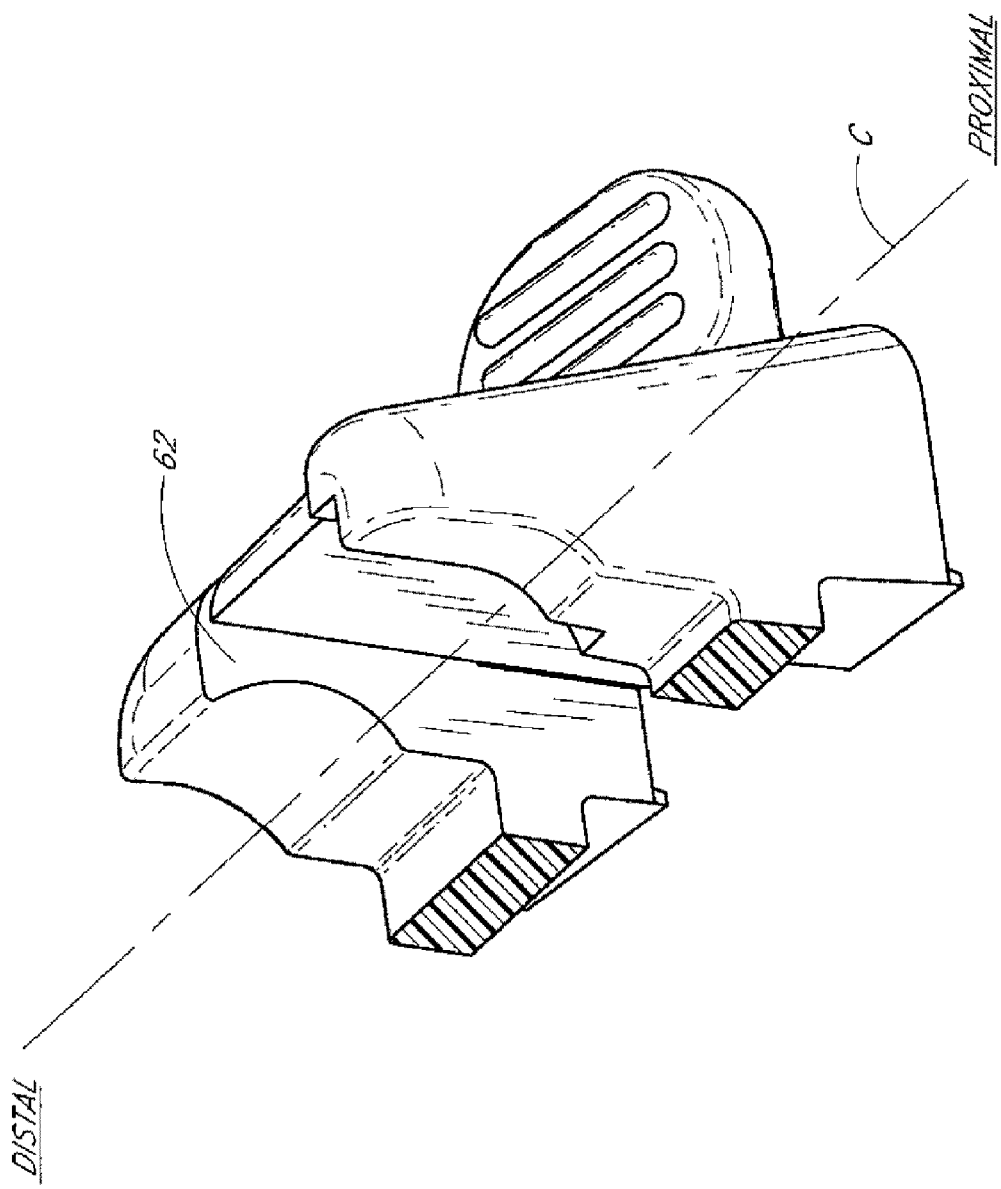
FIG. 20 is a isometric, cross-sectional view of the retainer of FIG. 15, taken along the 20-20 line.

As appreciated from FIGS. 13, 14, and 19, the upper edges 96 of the side walls 94 preferably are rounded or chamfered and slope toward the distal channel section 92 to guide the connector tubular body 34 into the channel 52. As a result, the connector 22 slides more smoothly over the upper edges 96 of the side walls 94 and into the channel.

The walls 94 preferably wrap around a sufficient amount of the connector 22 to inhibit unintentional transverse movement of the connector 22 relative to the retainer 300. As understood from the above description, the upper ends of the walls 94 curve inwardly to narrow the lateral width of the channel opening 56. The extent to which the upper ends can extend inward is limited, however, in order to permit insertion of the connector 22 into the channel 52 through the opening 56. Accordingly, the walls 94 preferably have a length sufficient to produce the desired retention strength to hold the connector 22 in the retainer 300 against an upwardly directed force (or force component).

Figure 18:
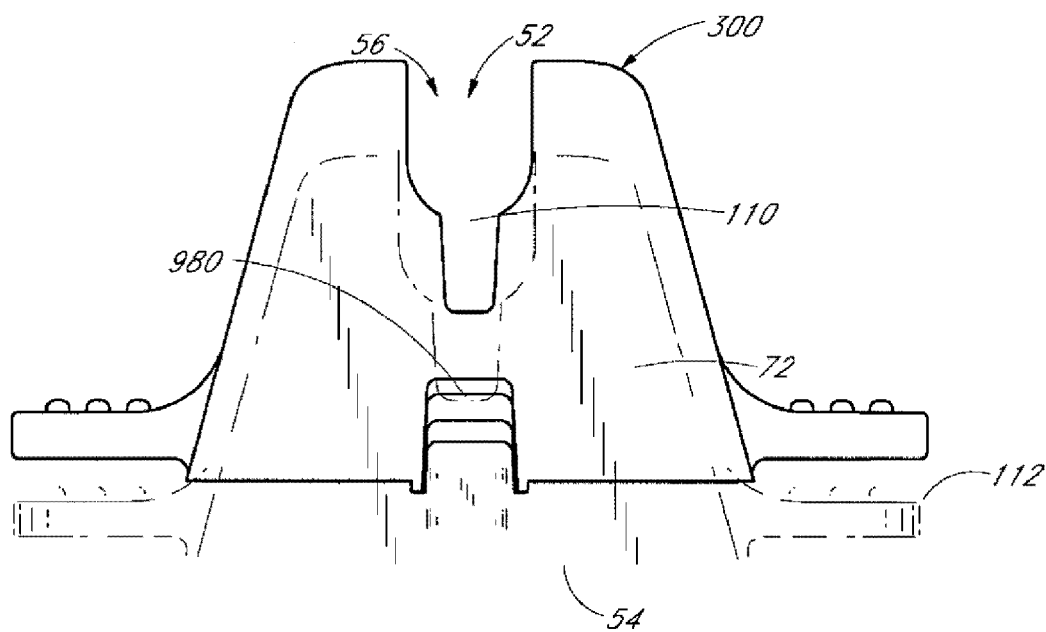
FIG. 18 is an elevational proximal end view of the retainer of FIG. 13.

As best seen in FIGS. 15 and 18, the proximal opening 110 and the proximal section 106 of the channel 52 are notched along their base. The resulting relief 980 extends transversely from the proximal opening 110 and the proximal section 106 towards the base surface 54 and longitudinally through the proximal end portion 72. In the illustrated embodiment, the relief 980 has a generally rectangular cross-sectional shape. The relief 980 also has a lateral width less than the diameter of the proximal section 106, and preferably has a lateral width approximately equal to one-quarter of the diameter of the proximal channel section 106. The decreased lateral thickness and the decrease transverse thickness of the proximal end portion 72 below the channel 52, as a result of the relief 980, provides increased flexibility to permit the walls of the proximal section 106 to deflect elastically outwardly when pressing the connector tubular body 34 into the channel 52.

Figure 16:
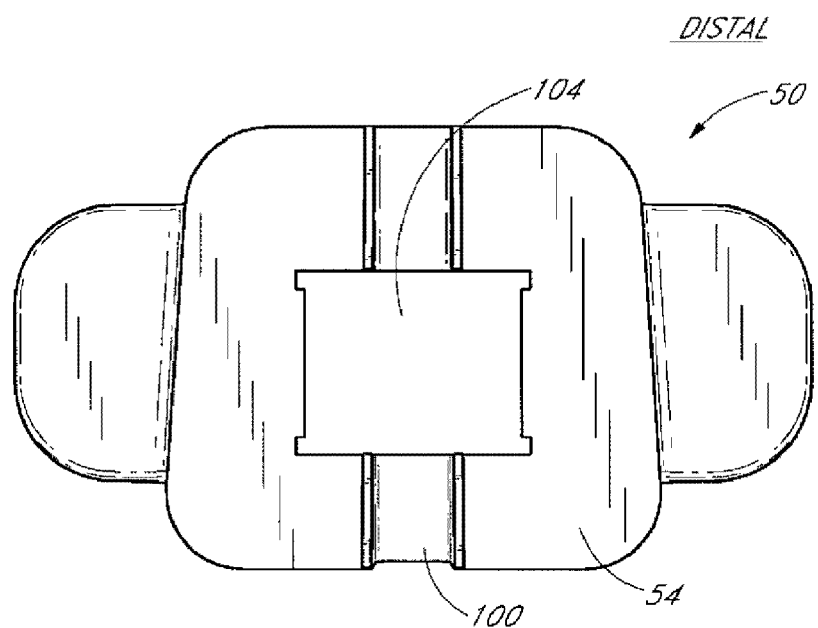
FIG. 16 is a bottom plan view of the retainer of FIG. 13.

As seen in FIG. 16, a recess 104 preferably is defined in the retainer body 50 at a point between the proximal and distal end portions 72, 74 and between the flexible walls 66, and extends toward the base surface 54 from the channel 52. In the illustrated embodiment, the recess 104 extends between the channel 52 and the base surface 54 in order to reduce the material weight of the retainer 300; however, the recess 104 need only be deep enough to receive one or more of the splines 44 that may extend downward when the connector 22 is inserted into the retainer 300.

The recess 104 is defined by a proximal wall and a distal wall. The distal wall is formed by a proximal end surface of the distal end portion 74 of the retainer 300 and the proximal wall is formed by a distal end surface of the proximal end portion 72 of the retainer 300. Both of these walls lie generally normal to the central axis c of the channel 52 and lie generally in an upright position. The spacing between the walls preferably is as long as the longitudinal length $L_1$ of the central spline 44a. In the illustrated embodiment, the distal wall forms a portion of the distal-most abutment surface 62, and the proximal wall forms a portion of the penult-proximate abutment surface 70. Accordingly, the distal-most abutment surface 62 is formed on the proximal ends of the side walls 94 of the distal end portion 74 and on the distal wall of the recess 104. The penult-proximate abutment surface 70 is formed on the proximal wall of the recess 104.

The proximal end portion 72 defines a proximal section 106 of the channel 52 between the penult-proximate abutment surface 70 and the proximal-most abutment surface 60. The proximal section 106 of the channel 52 generally has a U-shaped cross-section with a radius of curvature at least as large as the radius of the connector tubular body 34. The radius of curvature preferably is larger than the radius of the connector tubular body 34.

The proximal end portion 72 also includes a proximal upstanding wall 108 that extends laterally across the proximal end of the retainer 300. The upstanding wall 108 includes a U-shaped opening 110 that defines the proximal end of the channel 52. The opening 110 has a lateral width that is smaller than the diameter of the connector tubular body 34, but is larger than the diameter of the fluid tube 24. In the illustrated embodiment, the proximal upstanding wall 108 defines the proximal-most abutment surface 60 on its distal side. The proximal-most abutment surface 60 thus, in the illustrated embodiment, lies at the proximal end of the channel proximal section 106.

Both the proximal opening 110 and the proximal section 106 of the channel 52 have generally U-shapes; however, one or both of these channel sections can have a truncated, generally circular shape. In this variation, the opening or the proximal channel section can receive the fluid tube or the proximal end of the connector tubular body, respectively, in a snap fit manner, similar to the distal end portion of the retainer, to inhibit further transverse movement of the connector relative to the retainer.

Additional Method of Use

Figure 22B:
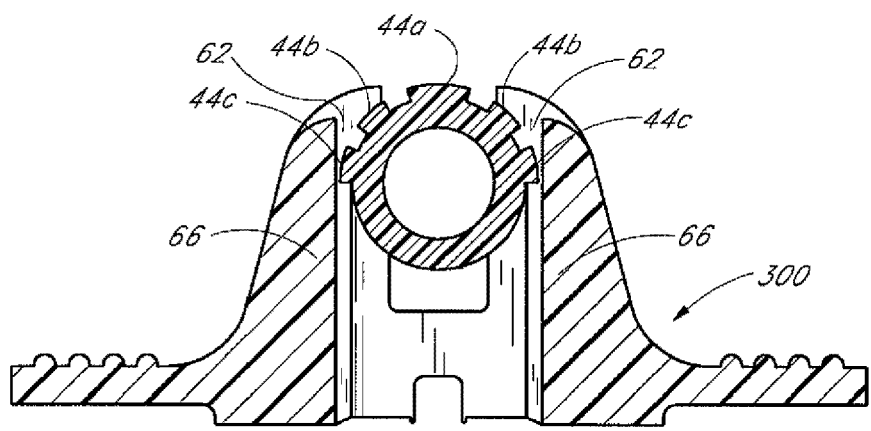
FIG. 22B is a cross-sectional view of the catheterization system of FIG. 22A, taken along the 22B-22B line.

The following discussion of the method of use is similar to the method of use described with reference to FIG. 11 except as described below. FIGS. 22A-D illustrate how the retainer 300 prevents the longitudinal movement of the connector 22 in both the proximal and distal directions once the connector 22 is positioned within the channel 52, irrespective of the position of the splines 44 when the connector 22 is inserted into the retainer 300. In FIGS. 22A and 22B, the connector 22 is situated such that the elongated spline 44a faces away from the retainer base surface 54. When the connector 22 is situated as such and the healthcare provider presses the connector 22 into the retainer 300, the diametrically opposed splines 44c slide into the recesses or spaces between the distal-most abutment surface 62 and the penult-proximate abutment surface 70. Once inserted fully, these abutment surfaces 62, 70 restrain the diametrically opposed splines 44c and thus inhibit longitudinal movement of the connector 22 in both the proximal and distal directions. A gap may exist between the distal ends of the splines 44c and the distal-most abutment surface 62 when the connector 22 is shifted in the proximal direction. A gap may exist between the proximal ends of the splines 44c and the penult-proximate abutment surface 70 when the connector 22 is shifted in the distal direction. This limited amount of play between the retainer 300 and the connector 22 can permit the healthcare provided to finely adjust the location of the connector 22 relative to the patient. However once the connector 22 is completely shifted in either the distal or proximal longitudinal direction, further movement in that direction is inhibited by the retainer 300.

When the connector 22 is placed within the retainer 300, walls 66 can contact one or more splines 44 and/or the body of the connector 22. The contact with the walls 66 provides a frictional force which further inhibits movement of the connector 22 in the longitudinal direction.

Figure 22C:
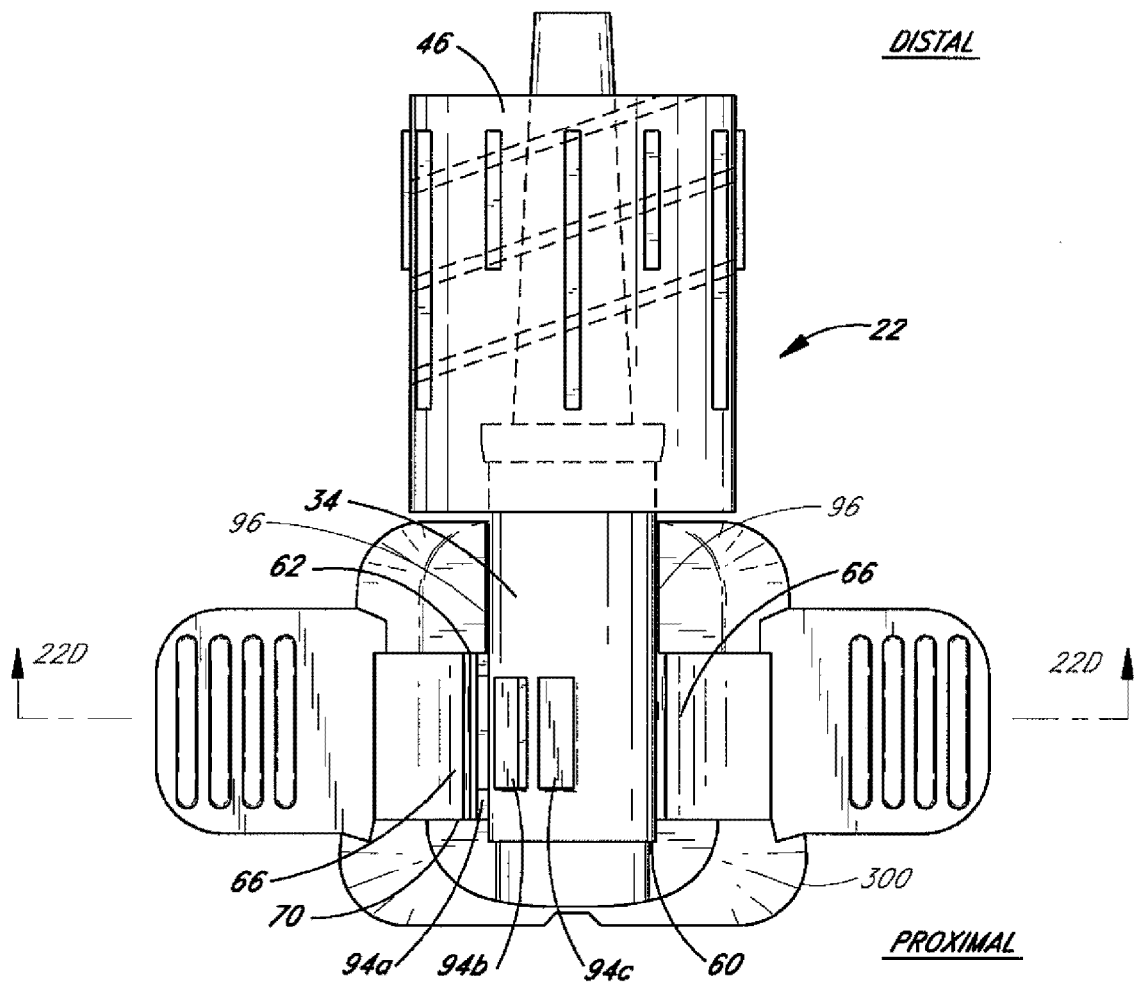
FIG. 22C is a top plan view of the catheterization system of FIG. 22A with the connector inserted with the splines rotated 90° from their position in FIG. 22A (the tubing also has been omitted in this drawing)
Figure 22D:
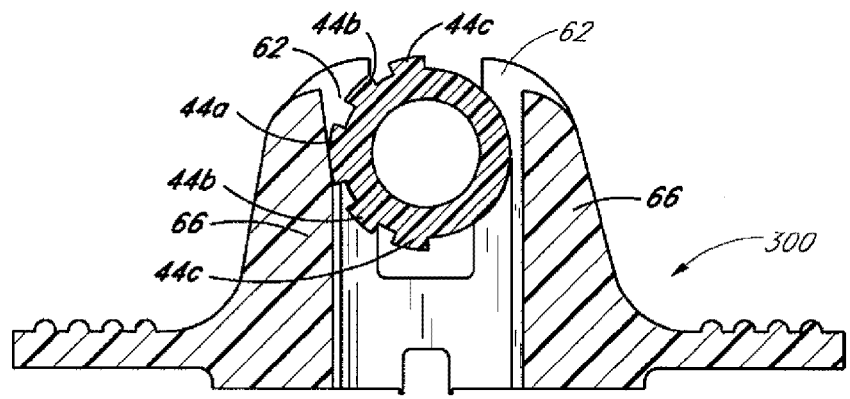
FIG. 22D is a cross-sectional view of the catheterization system of FIG. 22C including the retainer from FIG. 13, taken along the 22D-22D line.

In FIGS. 22C and 22D, the connector 22 is situated such that the elongated spline 44a is rotated about 90° from its position in FIG. 22A. The longitudinal ends of the elongated spline 44a fall between the penult-proximate abutment surface 70 and distal-most abutment surface 62. These abutment surfaces 70, 62 longitudinally restrain the elongated spline 44a and thus inhibit the longitudinal movement of the connector 22 relative to the retainer 300. In particular, the distal-most abutment surface 62, against which the distal end of the elongated spline 44a acts when moved distally, inhibits longitudinal movement of the connector 22 in the distal direction. The penult-proximate abutment surface 70, against which the proximal end of the elongated spline 44a acts when moved proximally, inhibits proximal movement of the connector 22 in the proximal direction.

The preceding scenarios merely illustrate the functioning of the retainer 300. As will be readily apparent to one skilled in the art, no matter what position the connector 22 and its splines 44 are in, at least one of the splines 44 is retained by one or more of the retainer's abutment surfaces and thus longitudinal movement of the connector is inhibited.

Additionally, the proximal-most abutment surface 60 arrests longitudinal movement of the connector 22 in the proximal direction irrespective of the positions of the connector splines 44 when the connector 22 is inserted into the retainer 300. The proximal end 38 of the connector 22 abuts or contacts the proximal-most abutment surface 60 of the retainer 300 in every rotational position of the connector 22. Accordingly, the proximal-most abutment surface 60 also inhibits proximal movement of the connector 22 along in the longitudinal direction.

The present anchoring system thus provide a sterile, tight-gripping, needle- and tape-free way to anchor a medical article to a patient. The retainer eliminates use of tape, and if prior protocol required suturing, it also eliminates accidental needle sticks, suture-wound-site infections and scarring. In addition, the retainer can be configured to be used with any of a wide variety of catheters, fittings, tubes, wires, and other medical articles. Patient comfort is also enhanced and application time is decreased with the use of the present anchoring system.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct anchoring systems in accordance with principles of the present invention.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present retainer has been described in the context of particularly preferred embodiments, the skilled artisan will appreciate, in view of the present disclosure, that certain advantages, features and aspects of the retainer may be realized in a variety of other applications, many of which have been noted above. For example, while particularly useful for small-scale applications, such as the illustrated medical application, the skilled artisan can readily adopt the principles and advantages described herein to a variety of other applications, including larger scale devices. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A method of releasably a anchoring medical article, the medical article having a generally elongated body and at least one spline that projects away from an outer surface of the body and along the length of the body, the method comprising:
    positioning a retainer below the medical article, the retainer having a first flexible wall and a second flexible wall both extending in a generally transverse direction and defining at least a portion of a channel, and an opening extending along the longitudinal axis and into the channel, each of the first and second walls being movable between an open position and a closed position and defining at least a portion of the opening, the opening having a greater lateral width when the first and second walls are in the open position than when the first and second walls are in the closed position;
    aligning the medical article with the retainer;
    passing at least a portion of the medical article through the opening;
    inserting the portion of the medical article passing through the opening into the channel;
    contacting the first wall with the spline;
    deflecting the first wall from the closed position to the open position due to the contact between the first wall and the spline; and
    limiting return of the first wall to the closed position through the interaction of the first wall with the spline.

2. The method of claim 1 further comprising positioning the spline between first and second abutment surfaces, each abutment surface facing in a proximal or distal direction.

3. The method of claim 2, wherein a distance between the first and second abutment surfaces generally corresponds to a longitudinal length of the spline.

4. The method of claim 1 further comprising contacting a proximal or distal facing abutment surface of the retainer with at least a portion of the spline so as to limit longitudinal movement of the medical article relative to the retainer.

5. The method of claim 1, wherein at least a portion of the retainer has a lateral thickness that is greater than a lateral thickness of each the first and second walls.

6. The method of claim 1 further comprising a first lateral slot and a second lateral slot, each slot being formed in the retainer and adjacent to the first and second walls.

7. The method of claim 1 further comprising providing an anchor pad upon which the retainer is disposed, the anchor pad having an adhesive disposed upon one side; and attaching the retainer to the skin of a patient.

8. The method of claim 1 further comprising pressing a pair of laterally extending platforms in the transverse direction so as to cause the first and second walls to move toward the open position.

9. A method of releasably anchoring a medical article, the medical article having a generally elongated body and at least first and second splines that project away from an outer surface of the body and along the length of the body, the method comprising:
  providing a retainer comprising a channel extending on a longitudinal axis between a proximal end portion and a distal end portion of the retainer and at least partially between two flexible walls, the two flexible walls extending in a transverse direction and movable between a first position relative to the proximal end portion and the distal end portion and a second position laterally displaced from the first position, the second position being disposed inward of the first position;
  positioning the retainer below the medical article;
  deflecting the first flexible wall to the first position through direct contact of the first spline with the first flexible wall;
  inserting at least a portion of the medical article into the channel;
  and returning the first flexible wall to the second position.

10. The method of claim 9 further comprising contacting a first abutment surface of the first flexible wall and a second abutment surface of the first flexible wall with the first spline so as limit the longitudinal movement of the medical article through.

11. The method of claim 10, wherein a distance between the first and second abutment surfaces generally corresponds to a longitudinal length of the first spline.

12. The method of claim 9, wherein a first slot is formed in the retainer between the proximal end portion and the first flexible wall and a second slot is formed in the retainer between the distal end portion and the first flexible wall, the first and second slots extending along a generally transverse axis.

13. The method of claim 12, wherein a longitudinal length of the second spline generally corresponds to a distance between the first slot and the second slot.

14. The method of claim 9 further comprising providing an anchor pad upon which the retainer is disposed, the anchor pad having an adhesive disposed upon one side; and attaching the retainer to the skin of a patient.

15. The method of claim 9 further comprising pressing a pair of laterally extending platforms in the transverse direction so as to cause the two flexible walls to be displaced outward along a lateral axis.

16. A method of releasably anchoring a medical article, the medical article having a generally elongated body and at least first and second splines that project away from an outer surface of the body and along the length of the body the method comprising:
  providing a retainer comprising a channel extending on a longitudinal axis between a proximal end portion and a distal end portion of the retainer and at least partially between two flexible walls, the two flexible walls extending in a transverse direction along the retainer and being disposed between the proximal and distal end portions, the two flexible walls being movable between a first position relative to the proximal and distal end portions and a second position laterally displaced from the first position, the second position being disposed inward of the first position, the retainer being configured to receive the medical article when the medical article is in either a first clocking corresponding to a first rotational orientation relative to the retainer or in a second clocking corresponding to a second rotational orientation relative to the retainer;
  positioning the retainer below the medical article;
  inserting at least a portion of the medical article into the channel; and
  when in the first clocking, securing the medical article by deflecting the first flexible wall toward the first position through contact between the first flexible wall and the first spline and positioning the first spline between a first abutment surface and a second abutment surface, the first abutment surface being disposed on the proximal end portion of the retainer and the second abutment surfacing being disposed on the distal end portion of the retainer, and
  when in the second clocking, securing the medical article by positioning the second spline between a first surface and a second surface, the first surface and the second surface being disposed on the two flexible walls.

17. The method of claim 16, wherein at least a portion of the retainer has a lateral thickness that is greater than a lateral thickness of the two flexible walls.

18. The method of claim 16, wherein a first slot is disposed the proximal end portion and the first flexible wall and a second slot is disposed between the distal end portion and the first flexible wall.

19. The method of claim 16, wherein a distance between the first and second abutment surfaces generally corresponds to a longitudinal length of the first spline.

20. The method of claim 16, wherein a distance between the first and second surfaces generally corresponds to a longitudinal length of the second spline.

* * * * *

UNITED STATES PATENT AND TRADEMARK OFFICE
CERTIFICATE OF CORRECTION

| | | |
|---|---|---|
| PATENT NO. | : 7,935,083 B2 | Page 1 of 1 |
| APPLICATION NO. | : 12/367442 | |
| DATED | : May 3, 2011 | |
| INVENTOR(S) | : Steven F. Bierman, Wayne T. Mitchell and Richard A. Pluth | |

It is certified that error appears in the above-identified patent and that said Letters Patent is hereby corrected as shown below:

In column 1, line 7, Change "2004" to --2004,--.

In column 11, line 8, Change "Toughy-Bourst" to --Touhy-Borst--.

In column 11, line 27, Change "44b." to --44b,--.

In column 12, line 19, Change "the extends" to --that extends--.

In column 19, line 49, Change "what ever" to --whatever--.

In column 21, line 44, Change "(FIG. 3-10)" to --(FIGS. 3-10)--.

In column 22, line 46, Change "the extends" to --that extends--.

In column 26, line 31, In Claim 1, change "a anchoring" to --anchoring a--.

Signed and Sealed this

Thirteenth Day of November, 2012

David J. Kappos
*Director of the United States Patent and Trademark Office*